US009856186B2

(12) United States Patent
Salciccioli et al.

(10) Patent No.: US 9,856,186 B2
(45) Date of Patent: *Jan. 2, 2018

(54) PRODUCTION AND USE OF DIALKYLBIPHENYL ISOMER MIXTURES

(71) Applicant: ExxonMobil Chemical Patents Inc., Baytown, TX (US)

(72) Inventors: Michael Salciccioli, Houston, TX (US); Jihad M. Dakka, Whitehouse Station, NJ (US); Emiel de Smit, Sint-Lambrechts-Woluwe (BE); Neeraj Sangar, League City, TX (US); Scott J. Weigel, Allentown, PA (US); Sumathy Raman, Annandale, NJ (US); Terry E. Helton, Montgomery, TX (US); Lorenzo C. DeCaul, Langhorne, PA (US); Christine N. Elia, Bridgewater, NJ (US); Chuansheng Bai, Phillipsburg, NJ (US); Ranjita Ghose, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 33 days.

This patent is subject to a terminal disclaimer.

(21) Appl. No.: 14/957,332

(22) Filed: Dec. 2, 2015

(65) Prior Publication Data

US 2016/0176785 A1 Jun. 23, 2016

Related U.S. Application Data

(60) Provisional application No. 62/094,218, filed on Dec. 19, 2014.

(51) Int. Cl.
| | | |
|---|---|---|
| C07C 2/66 | (2006.01) | |
| C07C 5/22 | (2006.01) | |
| C07C 5/32 | (2006.01) | |
| C07C 5/27 | (2006.01) | |
| C07C 2/74 | (2006.01) | |
| C07C 5/367 | (2006.01) | |
| C07C 2/86 | (2006.01) | |
| C07C 2/82 | (2006.01) | |

(52) U.S. Cl.
CPC ............. *C07C 5/2737* (2013.01); *C07C 2/66* (2013.01); *C07C 2/74* (2013.01); *C07C 2/82* (2013.01); *C07C 2/86* (2013.01); *C07C 5/367* (2013.01); *C07C 2101/14* (2013.01); *C07C 2521/02* (2013.01); *C07C 2521/04* (2013.01); *C07C 2521/10* (2013.01); *C07C 2529/08* (2013.01); *C07C 2529/18* (2013.01); *C07C 2529/40* (2013.01); *C07C 2529/70* (2013.01); *C07C 2529/78* (2013.01)

(58) Field of Classification Search
CPC ................ C07C 2/66; C07C 5/22; C07C 5/32
USPC ....... 585/319, 320, 321, 323, 480, 481, 482, 585/467, 440
See application file for complete search history.

(56) References Cited

U.S. PATENT DOCUMENTS

| | | |
|---|---|---|
| 2,520,084 A | 8/1950 | Dazzi |
| 2,634,248 A | 4/1953 | Dazzi |
| 2,976,266 A | 3/1961 | Lytton et al. |
| 3,296,065 A | 1/1967 | O'Brien et al. |
| 3,842,040 A | 10/1974 | Browne et al. |
| 3,842,041 A | 10/1974 | Browne et al. |
| 3,928,481 A | 12/1975 | Suggitt |
| 3,928,484 A | 12/1975 | Suggitt |
| 3,962,362 A | 6/1976 | Suggitt |
| 4,123,470 A | 10/1978 | Murtha |
| 4,218,572 A | 8/1980 | Dolhyj et al. |
| 4,263,457 A | 4/1981 | Takeda et al. |
| 4,294,976 A | 10/1981 | Itatani et al. |
| 4,463,207 A | 7/1984 | Johnson |
| 4,959,450 A | 9/1990 | Morris et al. |
| 5,001,296 A | 3/1991 | Howley et al. |
| 5,138,022 A | 8/1992 | Mang et al. |
| 6,037,513 A | 3/2000 | Chang et al. |
| 6,103,919 A | 8/2000 | Schiraldi et al. |
| 6,274,756 B1 | 8/2001 | Caers et al. |
| 6,355,711 B1 | 3/2002 | Godwin et al. |
| 6,433,236 B1 | 8/2002 | Schiraldi et al. |
| 6,482,972 B1 | 11/2002 | Bahrmann et al. |
| 6,730,625 B1 | 5/2004 | Chang et al. |
| 6,740,254 B2 | 5/2004 | Zhou et al. |
| 6,777,514 B2 | 8/2004 | Patil et al. |
| 7,297,738 B2 | 11/2007 | Gosse et al. |
| 8,829,093 B2 | 9/2014 | Dakka et al. |
| 2005/0137437 A1 | 6/2005 | Soloveichik et al. |
| 2005/0215433 A1 | 9/2005 | Benitez et al. |

(Continued)

FOREIGN PATENT DOCUMENTS

| | | |
|---|---|---|
| JP | 03-106833 A | 5/1991 |
| JP | 07-173086 A | 7/1995 |

(Continued)

OTHER PUBLICATIONS

U.S. Appl. No. 61/040,480, filed Mar. 28, 2008, Godwin.
U.S. Appl. No. 61/203,626, filed Dec. 24, 2008, Dakka et al.
U.S. Appl. No. 61/577,900, filed Dec. 20, 2011, Dakka et al.
U.S. Appl. No. 61/781,109, filed Mar. 14, 2013, Dakka et al.
U.S. Appl. No. 61/781,116, filed Mar. 14, 2014, Bai et al.
U.S. Appl. No. 61/781,129, filed Mar. 14, 2014, Dakka et al.
U.S. Appl. No. 61/781,137, filed Mar. 14, 2014, Dakka et al.
U.S. Appl. No. 61/781,728, filed Mar. 14, 2014, Dakka et al.
U.S. Appl. No. 62/012,024, filed Jun. 13, 2014, Salciccioli et al.

(Continued)

*Primary Examiner* — Thuan D Dang

(57) ABSTRACT

A process is described for converting at least one isomer of a dialkyl-substituted biphenyl compound, such as at least one 2,X' dialkylbiphenyl isomer (where X' is 2', 3' and/or 4'), into at least one different isomer, 3,3', 3,4' and/or 4,4' dialkylbiphenyl isomer. The process comprises contacting a feed comprising the dialkyl-substituted biphenyl compound isomer with an acid catalyst under isomerization conditions.

17 Claims, 11 Drawing Sheets

(56) References Cited

U.S. PATENT DOCUMENTS

| | | |
|---|---|---|
| 2006/0247461 A1 | 11/2006 | Schlosberg et al. |
| 2008/0242895 A1 | 10/2008 | Godwin et al. |
| 2009/0299111 A1 | 12/2009 | Kanbara et al. |
| 2010/0159177 A1 | 6/2010 | Dakka et al. |
| 2011/0151162 A1 | 6/2011 | Dakka et al. |
| 2011/0184105 A1 | 7/2011 | Dakka et al. |
| 2011/0215433 A1 | 9/2011 | Kokubun |
| 2012/0108726 A1 | 5/2012 | Godwin et al. |
| 2012/0108874 A1 | 5/2012 | Gralla et al. |
| 2012/0283494 A1 | 11/2012 | Smith et al. |
| 2014/0212666 A1 | 7/2014 | Dakka et al. |
| 2014/0272626 A1 | 9/2014 | Berlowitz et al. |
| 2014/0275605 A1 | 9/2014 | Dakka et al. |
| 2014/0275606 A1 | 9/2014 | Bai et al. |
| 2014/0275607 A1 | 9/2014 | Dakka et al. |
| 2014/0275609 A1 | 9/2014 | Dakka et al. |
| 2014/0315021 A1 | 10/2014 | Naert et al. |
| 2014/0316155 A1 | 10/2014 | Dakka et al. |
| 2014/0323782 A1 | 10/2014 | Chen et al. |
| 2014/0378697 A1 | 12/2014 | de Smit et al. |
| 2015/0080545 A1 | 3/2015 | Dakka et al. |
| 2015/0080546 A1 | 3/2015 | Dakka et al. |

FOREIGN PATENT DOCUMENTS

| | | |
|---|---|---|
| JP | 08-020548 A | 1/1996 |
| JP | 08-099914 | 4/1996 |
| SU | 412182 | 1/1974 |
| WO | WO 1999/32427 | 7/1999 |
| WO | WO 2003/029339 | 4/2003 |
| WO | WO 2004/046078 | 6/2004 |
| WO | WO 2007/013469 | 2/2007 |
| WO | WO 2010/138248 | 12/2010 |
| WO | WO 2011/096989 | 8/2011 |
| WO | WO 2011/096993 | 8/2011 |
| WO | WO 2012/082407 | 6/2012 |
| WO | WO 2014/159094 | 10/2014 |
| WO | WO 2014/159104 | 10/2014 |

OTHER PUBLICATIONS

U.S. Appl. No. 62/012,037, filed Jun. 13, 2014, Dakka et al.
U.S. Appl. No. 62/026,889, filed Jan. 27, 2015, Dakka et al.
U.S. Appl. No. 62/068,144, filed Oct. 24, 2014, Dakka et al.
U.S. Appl. No. 62/094,218, filed Dec. 19, 2014, Salciccioli et al.
U.S. Appl. No. 62/137,996, filed Mar. 25, 2015, Salciccioli et al.
U.S. Appl. No. 62/138,179, filed Mar. 25, 2015, Evans et al.
U.S. Appl. No. 62/140,723, filed Mar. 31, 2015, Salciccioli et al.
U.S. Appl. No. 13/316,745, filed Dec. 12, 2011, Patil et al.
U.S. Appl. No. 14/164,889, filed Jan. 27, 2014, Dakka et al.
U.S. Appl. No. 14/201,173, filed Mar. 7, 2014, Dakka et al.
U.S. Appl. No. 14/201,224, filed Mar. 7, 2014, Dakka et al.
U.S. Appl. No. 14/201,226, filed Mar. 7, 2014, Bai et al.
U.S. Appl. No. 14/201,284, filed Mar. 7, 2014, Dakka et al.
U.S. Appl. No. 14/201,287, filed Mar. 7, 2014, Dakka et al.
U.S. Appl. No. 14/480,363, filed Sep. 8, 2014, Dakka et al.
U.S. Appl. No. 14/486,945, filed Sep. 15, 2014, Dobin et al.
U.S. Appl. No. 14/516,239, filed Oct. 16, 2014, Dakka et al.
U.S. Appl. No. 14/527,480, filed Oct. 29, 2014, Patil et al.
Bandyopadhyay et al., "*Transalkylation of cumene with toluene over zeolite Beta*," Applied Catalysis A: General, 1996, vol. 135(2), pp. 249-259.
Bandyopadhyay et al., "*Transalkylation reaction—An alternative route to produce industrially important intermediates such as cymene*," Catalysis Today, 1998, vol. 44, pp. 245-252.
Borodina et al., "Hydroalkylation of Benzene and Ethylbenzene over Metal-Containing Zeolite Catalysts," Petroleum Chemistry, 2009, vol. 49(1), pp. 66-73.
Clary et al., "*A Green, One-Pot Route to the Biphenyldicarboxylic Acids: Useful Intermediates in Polymer Synthesis*," International Journal of Organic Chemistry, Jun. 2013, vol. 3(2), pp. 143-147.
Ennis et al., "*Multikilogram-Scale Synthesis of a Biphenyl Carboxylic Acid Derivative Using a Pd/C-Mediated Suzuki Coupling Approach*," Organic Process Research & Development, 1999, vol. 3(4), pp. 248-252.
Godwin, et al., "*Plasticizers*," Applied Polymer Science: $21^{st}$ Century, Elsevier, 2000, pp. 157-175.
Guo, et al., "*Reactivity of 4,4'-Dimethylbiphenyl with Methanol over modified HZSM-5 Catalysts*," PrePrints—American Chemical Society, Division of Petroleum Chemistry, 2003, vol. 48(4), pp. 280-282.
Hoefnagel et al., "Selective alkylation of methylbenzenes with cyclohexene catalyzed by solid acids," Catalysis Letters, vol. 85, No. 1-2, 2003, pp. 7-11.
Izard, "Effect of Chemical Structure on Physical Properties of Isomeric Polyesters," Journal of Polymer Science, 1952, vol. 9(1), 35-39.
Khromov et al., "*Catalytic Conversion of 1,1'-Dimethyldicyclohexyl and 1-Methyl-1-Phenyl-Cyclohexane on Platinum Catalysts at Elevated Hydrogen Pressures and Temperatures*," Vestnik Moskovskogo Universiteta, Seriya 2: Khimiya (1965), 20(1), 51-5, (English AbstractOnly).
Krigbaum et al., "Aromatic Polyesters Forming Thermotropic Smectic Mesophases," Journal of Polymer Science, Part C, Polymer Letters Edition, 1982, vol. 20(2), pp. 109-115.
Kulev et al., "*Esters of diphenic acid and their plasticizing properties*," Izvestiya Tomskogo Politekhnicheskogo Instituta, 1961, vol. 111 (Abstract).
Lagidze et al., "*Analysis of Substances Produced by Reaction Between Aluminum Chloride and Diphenyl in Dearomatized Ligroin*," V.I. Leni-n Georgian Polytechnic Institute (1968), No. 2 (122), pp. 36-44. (English Translation).
Lu et al., "Selective Hydrogenation of Single Benzene Ring in Biphenyl Catalyzed by Skeletal Ni," ChemCatChem., 2009, vol. 1(3), pp. 369-371.
Mavrodinova et al., "Transalkylation of toluene with cumene over zeolites Y dealuminated in solid-state, Part I. Effect of the alteration of Broensted acidity," Applied Catalysis A: General, 2003, vol. 248, pp. 181-196.
Mavrodinova et al., "Transalkylation of toluene with cumene over zeolites Y dealuminated in solid-state Part II. Effect of the introduced Lewis acid sites," Applied Catalysis A: General, 2003, vol. 248, p. 197-209.
Meurisse et al., "Polymers with Mesogenic Elements and Flexible Spacers in the Main Chain: Aromatic-Aliphatic Polyesters," British Polymer Journal, 1981, vol. 13(2), pp. 55-63.
Mukhopadhyay et al., "*Tandem One-Pot Palladium-Catalyzed Reductive and Oxidative Coupling of Benzene and Chlorobenzene*," Journal of Organic Chemistry, 2000, vol. 65(10), pp. 3107-3110.
Roux et al., "Critically Evaluated Thermochemical Properties of Polycyclic Aromatic Hydrocarbons," Journal of Physical and Chemical Reference Data, 2008, vol. 37(4), pp. 1855-1996.
Sherman et al., "Dimethylbiphenyls from toluene," American Chemical Society, Chemical Innovation, 2000, pp. 25-30.
Shioda et al., "*Synthesis of dialkyl diphenates and their properties*," Yuki Gosei Kagaku Kyokaishi 1959, 17. (Abstract).
Sinfelt, "The turnover frequency of methylcyclohexane dehydrogenation to toluene on a Pt reforming catalyst," Journal of Molecular Catalysis A: Chemical, 2000, vol. 163, pp. 123-128.
Sinfelt et al., "Kinetics of Methylcyclohexane Dehydrogenation Over PT-$Al_2O_3$," Journal of Physical Chemistry, 1960, vol. 64(10), 1559-1562.
Singh, et. al, "*Studies on Isomer Distribution in the Products Obtained by Friedelcrafts Alkylation of Toluene with Cyclic Electrophiles*," National Academy Science Letters, 1983, vol. 6(10), pp. 321-325.
Zhang, et al., "Automation of Fluorous Solid-Phase Extraction for Parallel Synthesis," J. Comb. Chem, 2006, vol. 8, pp. 890-896.

PRODUCTION AND USE OF DIALKYLBIPHENYL ISOMER MIXTURES

PRIORITY

This invention claims priority to and the benefit of U.S. Ser. No. 62/094,218, filed Dec. 19, 2014.

FIELD OF THE INVENTION

This invention relates to a production and use of dialkylbiphenyl isomers and, in particular, to a process for preparing a mixture of dimethylbiphenyl isomers, having an increased concentration of the 3,3', 3,4' and 4,4' isomers, and to use of the resultant mixture in the production of polyesters and plasticizers.

BACKGROUND OF THE INVENTION

Dimethylbiphenyl (DMBP) and other dialkylbiphenyls are useful intermediates in the production of a variety of commercially valuable products, including polyesters and plasticizers for PVC and other polymer compositions. For example, DMBP can readily be converted to an ester plasticizer by a process comprising oxidation of the DMBP to produce the corresponding mono- or dicarboxylic acid followed by esterification with a long chain alcohol. However, for certain uses, it is important to reduce the level of 2,X' DMBP (where X' is 2', 3' and 4') isomers in the product since, for example, diphenate esters having substitution on the 2-carbons tend to be too volatile for use as plasticizers.

In addition, 4,4'-diphenyl-dicarboxylic acid, optionally together with diphenyl-3,4'-dicarboxylic acid, is a potential precursor, either alone or as a modifier for polyethylene terephthalate (PET), in the production of polyester fibers, engineering plastics, liquid crystal polymers for electronic and mechanical devices, and films with high heat resistance and strength.

Homopolyesters of 4,4'-biphenyl dicarboxylic acid (BDA) and various aliphatic diols have been disclosed in the literature. For example, in the *Journal of Polymer Science*, 9, 35 (1952), Ezard discloses homopolyesters of 4,4'-biphenyl dicarboxylic acid and ethylene glycol. Similarly, in the *British Polymer Journal*, 13, 57 (1981), Meurisse et al. disclose homopolyesters made from 4,4'-biphenyl dicarboxylic acid and a number of diols including ethylene glycol, 1,4-butanediol and 1,6-hexanediol. Homopolyesters of 4,4'-biphenyl dicarboxylic acid and ethylene glycol are also disclosed in, for example, U.S. Pat. Nos. 3,842,040 and 3,842,041.

Copolyesters of 4,4'-biphenyl dicarboxylic acid with mixtures of aliphatic diols are also disclosed in the literature, see for example, in U.S. Pat. No. 2,976,266. In addition, in U.S. Pat. No. 4,959,450, Morris et al. disclose copolyesters from 4,4'-biphenyl dicarboxylic acid and mixtures of 1,4-cyclohexanedimethanol and 1,6-hexanediol. Copolyesters of 4,4'-biphenyl dicarboxylic acid and terephthalic acid with certain aliphatic diols are also disclosed in the literature, for example, in the *Journal of Polymer Science, Polym. Letters*, 20, 109 (1982) by Krigbaum et al. Moreover, U.S. Pat. No. 5,138,022 discloses copolyesters of 3,4' biphenyl dicarboxylic acid and optionally 4,4'-biphenyl dicarboxylic acid, and certain aliphatic diols, like ethylene glycol, 1,4-butanediol, and 1,4-cyclohexanedimethanol.

As disclosed in our co-pending U.S. patent application Ser. Nos. 14/201,287 and 14/201,224, both filed Mar. 7, 2014, dimethyl biphenyl may be produced by hydroalkylation of toluene followed by dehydrogenation of the resulting (methylcyclohexyl)toluene (MCHT). However, even using a selective molecular sieve catalyst for the hydroalkylation step, this process tends to yield a mixture of all six DMBP isomers, namely 2,2', 2,3' 2,4', 3,3', 3,4' and 4,4' DMBP, in which the 2,X' (where X' is 2', 3' or 4') and 3,3' DMBP isomer content may be 50% by weight or more of the total DMBP product. The entire disclosures of U.S. patent application Ser. Nos. 14/201,287 and 14/201,224 are incorporated herein by reference in their entirety.

Alternative routes to DMBP via benzene are described in co-pending U.S. patent application Ser. No. 14/164,889, filed Jan. 27, 2014, in which the benzene is initially converted to biphenyl, either by oxidative coupling or by hydroalkylation to cyclohexyl benzene (CHB) followed by dehydrogenation of the CHB, and then alkylation of the biphenyl with methanol. Again, however, the alkylated product is a mixture of DMBP isomers, in which the levels of the desired 3,4' and 4,4' isomers may be lower than 50% by weight of the total DMBP product.

Other references of interest include: U.S. Pat. No. 8,829,093; U.S. patent application Ser. Nos. 14/486,945, 14/480,363, 14/527,480, 13/316,745, 62/012,024, 62/012,037, and 62/068,144; and U.S. Patent Publication Nos. 2014-0212666, 2014-0316155, 2014-0275606, 2014-0275609, and 2014-0275605.

There is, therefore, interest in developing a process for producing dialkyl-substituted biphenyl compounds in which the yield of the 3,4' isomer, and particularly the 4,4' isomer, is maximized. At the same time, for acceptable process carbon efficiencies, it is important to utilize the 2,X' isomer content. In other embodiments, it may be desirable to enhance the concentration of other isomers, even the 2,X' isomers, in a mixture of dialkyl-substituted biphenyl compounds.

SUMMARY OF THE INVENTION

According to the present invention, it has now been found that the isomer distribution of dialkyl-substituted biphenyl compounds can be modified by reaction in the presence of an acid catalyst, particularly a solid phase acid catalyst, such as a molecular sieve. Also by suitable selection of the catalyst and the reaction conditions, the isomerization reaction can be conducted with little or no cracking of the dialkyl-substituted biphenyl species and with low conversion of unreacted MCHT and other cycloalkyl-containing compounds that may be present in the isomerization feed.

Thus, in one aspect, the invention resides in a process for converting at least one isomer of a dialkyl-substituted biphenyl compound into at least one different isomer, the process comprising contacting a feed comprising the dialkyl-substituted biphenyl compound isomer with an acid catalyst under isomerization conditions.

In a further aspect, the invention resides in a process for producing 3,3', 3,4' and/or 4,4' dialkylbiphenyl compounds, the process comprising:
  (a1) contacting a feed comprising one or more 2,X' dialkylbiphenyl isomers (where X' is 2', 3' and/or 4') with an acid catalyst under isomerization conditions effective to convert at least some of the 2,X' dialkylbiphenyl isomers to one or more 3,3', 3,4' and 4,4' dialkylbiphenyl isomers and produce an isomerization product.

In another aspect, the invention resides in a process for producing 3,3', 3,4' and/or 4,4' dialkylbiphenyl compounds, the process comprising:

(a2) contacting toluene with hydrogen in the presence of a hydroalkylation catalyst under conditions effective to produce a hydroalkylation product comprising (methylcyclohexyl)toluenes;

(b2) dehydrogenating at least part of the hydroalkylation product under conditions effective to produce a dehydrogenation product comprising dimethylbiphenyl isomers and unreacted (methylcyclohexyl)toluenes;

(c2) separating the dehydrogenation product into a first fraction comprising one or more 3,3', 3,4' and 4,4' dimethylbiphenyl isomers and a second fraction comprising one or more 2,X'-dimethylbiphenyl isomers (where X' is 2, 3 or 4) and at least part of the unreacted (methylcyclohexyl)toluenes;

(d2) contacting at least part of the second fraction with an acid catalyst under isomerization conditions effective to convert at least some of the 2,X' dialkylbiphenyl isomers to one or more 3,3', 3,4' and 4,4' dialkylbiphenyl isomers and produce an isomerization product; and (e2) recycling at least part of the isomerization product to the separating (c2).

This invention also relates to a process for producing 3,3', 3,4' and/or 4,4' dimethylbiphenyl compounds, the process comprising:

(a3) contacting toluene with hydrogen in the presence of a hydroalkylation catalyst under conditions effective to produce a hydroalkylation product comprising (methylcyclohexyl)toluenes;

(b3) dehydrogenating at least part of the hydroalkylation product under conditions effective to produce a dehydrogenation product comprising dimethylbiphenyl isomers and unreacted (methylcyclohexyl)toluenes;

(c3) supplying at least part of the dehydrogenation product to a separation zone to recover a first fraction enriched in one or more 3,3', 3,4' and/or 4,4' dimethylbiphenyl isomers as compared with the dehydrogenation product and a second fraction enriched in one or more of 2,X' dimethylbiphenyl isomers (where X' is 2', 3' and/or 4') as compared with the dehydrogenation product and also containing at least part of the unreacted (methylcyclohexyl)toluenes; and (d3) supplying at least part of the second fraction as at least part of a feed to an isomerization process comprising contacting the feed comprising one or more 2,X' dimethylbiphenyl isomers with an acid catalyst under isomerization conditions effective to convert at least some of the 2,X' dimethylbiphenyl isomers into one or more 3,3', 3,4' and 4,4' dimethylbiphenyl isomers and produce an isomerization effluent.

This invention also relates to a process for producing 3,3', 3,4' and/or 4,4' dimethylbiphenyl compounds, the process comprising:

(a4) contacting biphenyl with a methylating agent in the presence of an alkylation catalyst under conditions effective to produce a methylation reaction product comprising a mixture of dimethyl-substituted biphenyl isomers;

(b4) supplying at least part of the methylation reaction product to a separation zone to recover a first fraction enriched in one or more 3,3', 3,4' and 4,4' dimethylbiphenyl isomers as compared with the methylation reaction product and a second fraction enriched in one or more of 2,X' dimethylbiphenyl isomers (where X' is 2', 3' and/or 4') as compared with the methylation reaction product; and (c4) supplying at least part of the second fraction as at least part of a feed to an isomerization process comprising contacting the feed comprising one or more 2,X' dimethylbiphenyl isomers with an acid catalyst under isomerization conditions effective to convert at least some of the 2,X' dimethylbiphenyl isomers into one or more 3,3', 3,4' and 4,4' dimethylbiphenyl isomers and produce an isomerization effluent.

This invention also relates to a process for producing 3,3', 3,4' and/or 4,4' dimethylbiphenyl compounds, the process comprising:

(a5) contacting toluene with hydrogen in the presence of a hydroalkylation catalyst under conditions effective to produce a hydroalkylation product comprising (methylcyclohexyl)toluenes;

(b5) dehydrogenating at least part of the hydroalkylation product under conditions effective to produce a dehydrogenation product comprising dimethylbiphenyl isomers and unreacted (methylcyclohexyl)toluenes;

(c5) separating the dehydrogenation product into a first fraction comprising one or more 3,3', 3,4' and 4,4' dimethylbiphenyl isomers and a second fraction comprising one or more 2,X' dimethylbiphenyl isomers (where X' is 2, 3 or 4) and at least part of the unreacted (methylcyclohexyl)toluenes;

(d5) contacting at least part of the second fraction with an acid catalyst under isomerization conditions effective to convert at least some of the 2,X' dimethylbiphenyl isomers into one or more 3,3', 3,4' and 4,4' dimethylbiphenyl isomers and produce an isomerization product;

(e5) recycling at least part of the isomerization product to the separating (c5); (f5) optionally, separating the first fraction into a third fraction enriched in one target isomer selected from 3,3', 3,4' and 4,4' dimethylbiphenyl and a fourth fraction depleted in said target isomer;

(g5) contacting at least part of the fourth fraction with an acid catalyst under isomerization conditions effective to produce an isomerization product having an increased concentration of the target isomer as compared with the fourth fraction; and (h5) recycling at least part of the isomerization product to the separating (f5).

DETAILED DESCRIPTION OF THE EMBODIMENTS

Described herein is a process for isomerizing dialkylbiphenyl compounds. In particular, the present invention provides a process for the production of a mixture of dialkylbiphenyl isomers in which the amount of the 3,3', 3,4' and 4,4'-dialkylbiphenyl isomers is maximized and the amount of the 2,X' dialkylbiphenyl isomers (where X' is 2', 3' and/or 4') is minimized. In one embodiment, each alkyl group is a methyl moiety and the process is directed to converting 2,X' dimethylbiphenyl compounds to 3,3', 3,4' and 4,4' dimethylbiphenyl compounds useful as precursors in the manufacture of polyesters and biphenyl ester plasticizers.

By way of illustration, the 3,3', 3,4' and 4,4'-isomers of dimethylbiphenyl are shown below in formulas (I) to (III) respectively, whereas the 2,2', 2,3' and 2,4'-isomers are shown in formulas (IV) to (VI) respectively:

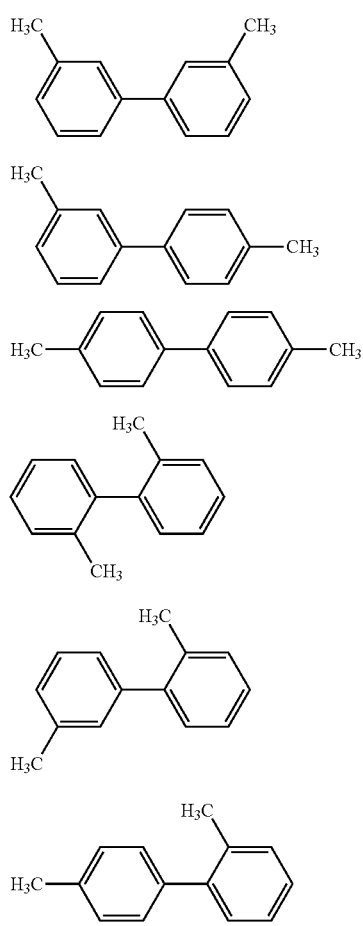

Figure 1:
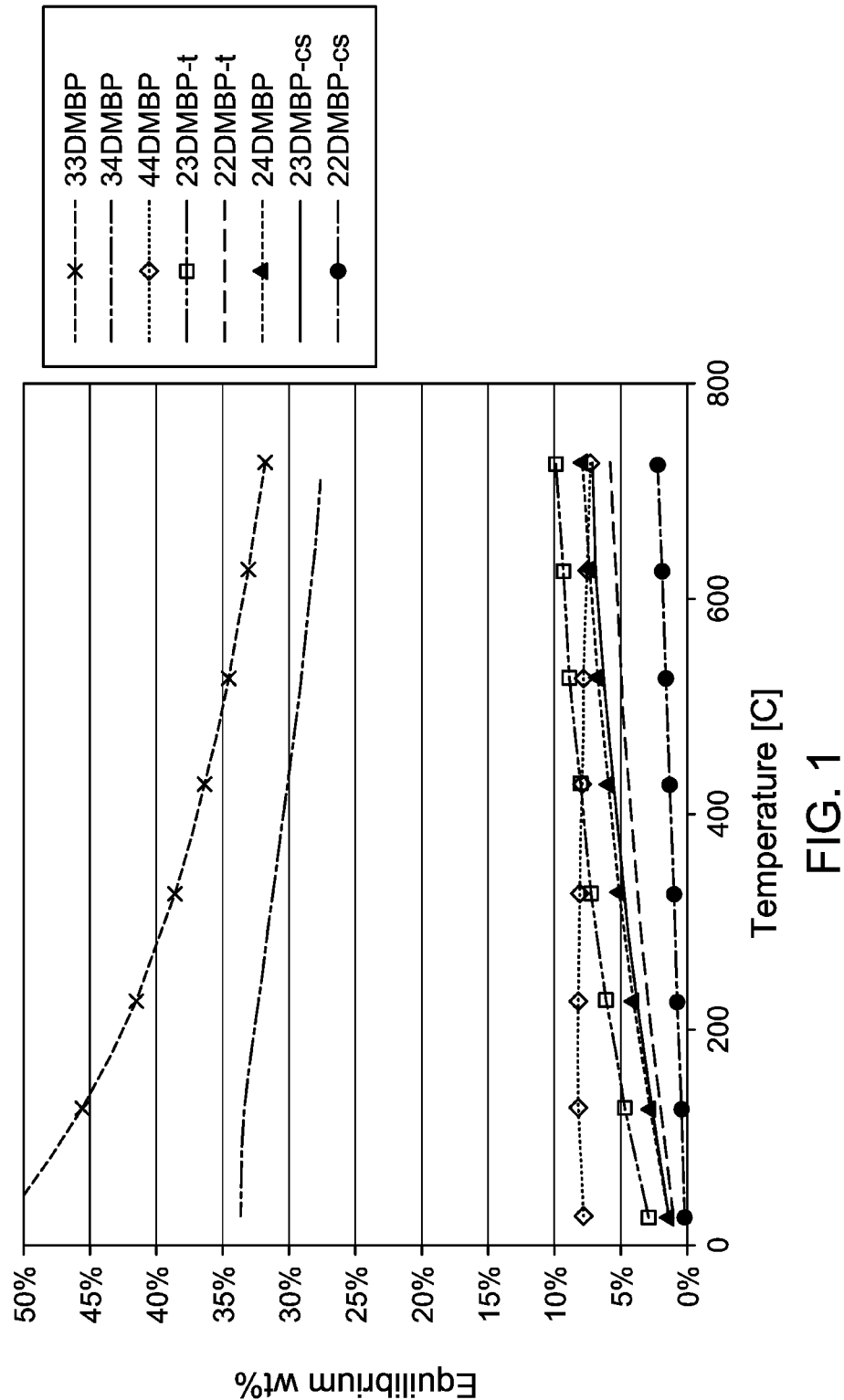
FIG. 1 is a graph showing the calculated equilibrium distribution of dimethylbiphenyl isomers over a temperature range from 20 to 750° C.

FIG. 1 is a graph showing the equilibrium distribution of the different isomers of dimethylbiphenyl shown in formulas (I) to (VI) at various temperatures from 0 to 750° C. based on thermochemical calculations assuming ideal gas-like behavior for the molecules. It will be seen that, at all temperatures within the range investigated, the most prevalent isomers are 3,3' and 3,4' dimethylbiphenyl, which are generally present in an amount from 30 to 55 wt % and 25 to 35 wt %, respectively, of the total isomer concentration. However, in all cases, significant quantities of all the other isomers are shown to be present, with the amount of 2,X' dimethylbiphenyl isomers typically ranging from 10 to 30 wt % of the total isomer concentration. For the manufacture of polyesters and biphenyl ester plasticizers, a desirable isomer is 4,4' dimethylbiphenyl. It will be seen from FIG. 1 that 4,4' dimethylbiphenyl is normally present in amounts less than 15 wt % of the total isomer concentration, demonstrating the importance of a process for converting the 2,X' dimethylbiphenyl isomers to the preferred 3,3', 3,4' and 4,4'-isomers.

In one embodiment, the present process comprises contacting a feed comprising one or more 2,X' dialkylbiphenyl isomers as shown in formulas (IV) to (VI) with an acid catalyst under isomerization conditions effective to convert at least some of the 2,X' dialkylbiphenyl isomers in the feed to one or more 3,3', 3,4' and 4,4' dialkylbiphenyl isomers as shown in formulas (I) to (III) and thereby produce an isomerization product. In one embodiment, the feed comprises a dialkylbiphenyl isomer mixture which is deficient in one or more of the 3,3', 3,4' and 4,4' isomers as a result of at least one prior separation step. For example, selective crystallization can be employed to recover at least part of the 4,4' dimethylbiphenyl isomer by virtue of its higher melting point than the other dimethylbiphenyl isomers. As can be seen from Table 1, which summarizes the normal boiling points and temperatures of fusion of various dimethylbiphenyl isomers, other separation steps, such as distillation, can be used to recover one or more of the 3,3', 3,4' and 4,4' dialkylbiphenyl isomers in the feed.

TABLE 1

| Isomer | Normal Boiling Point (K) | Fusion Temperature (K) |
|---|---|---|
| 2,2' | 531 | 320 |
| 2,3' | 546 | |
| 2,4' | 554 | |
| 3,3' | 559 | 278 |
| 3,4' | 569 | 283 |
| 4,4' | 568 | 394 |

Thus, for example, after selective crystallization to recover at least part of the 4,4' dimethylbiphenyl isomer, distillation or additional selective crystallization can be used to recover at least part of the 3,3' and 3,4'.

Any acid catalyst can be used to effect isomerization of the dialkylbiphenyl compounds in the feed to the present process. In most embodiments, the catalyst is a heterogeneous solid acid catalyst, such as a metal oxide, a clay or, more preferably, a molecular sieve. Particularly suitable molecular sieves are those having a Constraint Index (as defined in U.S. Pat. No. 4,016,218) less than 2, especially molecular sieves selected from the group consisting of BEA, FAU and MOR structure type molecular sieves and mixtures thereof.

The conditions used to effect isomerization of the dialkylbiphenyl-containing feed according to the present process are not closely controlled, but suitably include a temperature from 100° C. to 450° C., such as 100° C. to 250° C. and a pressure from 2 to 7,000 kPa-a, such as from 100 to 2000 kPa-a. In some embodiments, it may be desirable to select the temperature and pressure such as to maintain the dialkylbiphenyl components of the feed substantially in the liquid phase since this may reduce carbon losses resulting from cracking.

Any dialkylbiphenyl-containing feed can be used in the present process but, in one embodiment, the feed comprises a mixture of dimethylbiphenyl isomers produced from toluene by a combination of hydroalkylation followed by dehydrogenation. In this embodiment, the toluene is initially converted to (methylcyclohexyl)toluenes over a hydroalkylation catalyst according to the following reaction:

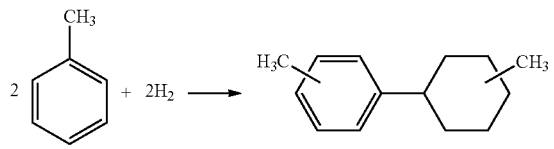

The catalyst employed in the hydroalkylation reaction is a bifunctional catalyst comprising a hydrogenation component and a solid acid alkylation component, typically a molecular sieve. The catalyst may also include a binder such as clay, alumina, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Ga. and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Any known hydrogenation metal or compound thereof can be employed as the hydrogenation component of the hydroalkylation catalyst, although suitable metals include palladium, ruthenium, nickel, zinc, tin, cobalt, silver, gold, platinum and compounds and mixtures thereof, with palladium being particularly advantageous. In certain embodiments, the amount of hydrogenation metal present in the catalyst is between about 0.05 and about 10 wt %, such as between about 0.1 and about 5 wt %, of the catalyst.

In one embodiment, the solid acid alkylation component comprises a large pore molecular sieve having a Constraint Index (as defined in U.S. Pat. No. 4,016,218) less than 2. Suitable large pore molecular sieves include zeolite beta, zeolite Y, Ultrastable Y (USY), Dealuminized Y (Deal Y), mordenite, ZSM-3, ZSM-4, ZSM-18, and ZSM-20. Zeolite ZSM-4 is described in U.S. Pat. No. 4,021,447. Zeolite ZSM-20 is described in U.S. Pat. No. 3,972,983. Zeolite Beta is described in U.S. Pat. No. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Mordenite is a naturally occurring material but is also available in synthetic forms, such as TEA-mordenite (i.e., synthetic mordenite prepared from a reaction mixture comprising a tetraethyl-ammonium directing agent). TEA-mordenite is disclosed in U.S. Pat. Nos. 3,766,093 and 3,894,104. Preferred large pore molecular sieves for use as the solid acid alkylation component of the hydroalkylation catalyst comprise molecular sieves of the BEA and FAU structure type.

In another, more preferred embodiment, the solid acid alkylation component comprises a molecular sieve of the MCM-22 family. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697) and mixtures thereof.

In addition to the toluene and hydrogen, a diluent, which is substantially inert under hydroalkylation conditions, may be included in the feed to the hydroalkylation reaction. In certain embodiments, the diluent is a hydrocarbon, in which the desired cycloalkylaromatic product is soluble, such as a straight chain paraffinic hydrocarbon, a branched chain paraffinic hydrocarbon, and/or a cyclic paraffinic hydrocarbon. Examples of suitable diluents are decane and cyclohexane. Although the amount of diluent is not narrowly defined, desirably the diluent is added in an amount such that the weight ratio of the diluent to the aromatic compound is at least 1:100; for example at least 1:10, but no more than 10:1, desirably no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa. The molar ratio of hydrogen to aromatic feed, such as toluene, is typically from about 0.15:1 to about 15:1.

In the present process, it is found that MCM-22 family molecular sieves are particularly active and stable catalysts for the hydroalkylation of toluene. In addition, catalysts containing MCM-22 family molecular sieves exhibit improved selectivity to the 3,3'-dimethyl, the 3,4'-dimethyl, the 4,3'-dimethyl and the 4,4'-dimethyl isomers in the hydroalkylation product, while at the same time reducing the formation of fully saturated and heavy by-products. For example, using an MCM-22 family molecular sieve with a toluene feed, it is found that the hydroalkylation reaction product may comprise:

- at least 60 wt %, such as at least 70 wt %, for example at least 80 wt % of the 3,3', 3,4', 4,3' and 4,4'-isomers of (methylcyclohexyl)toluene based on the total weight of all the (methylcyclohexyl)toluene isomers;
- less than 40 wt %, such as less than 30 wt %, for example from 15 to 25 wt % of the 2,2', 2,3', and 2,4'-isomers of (methylcyclohexyl)toluene based on the total weight of all the (methylcyclohexyl)toluene isomers;
- less than 30 wt % of methylcyclohexane and less than 2% of dimethylbicyclohexane compounds; and
- less than 1 wt % of compounds containing in excess of 14 carbon atoms.

The hydroalkylation reaction product may also contain significant amounts of residual toluene, for example up to 50 wt %, such as up to 90 wt %, typically from 60 to 80 wt % of residual toluene based on the total weight of the hydroalkylation reaction product. Thus, the major components of the hydroalkylation reaction effluent are (methylcyclohexyl)toluenes, residual toluene and fully saturated single ring by-product (methylcyclohexane). The residual toluene and light by-products can readily be removed from the reaction effluent by, for example, distillation. The residual toluene can then be recycled to the hydroalkylation reactor, while the saturated by-products can be dehydrogenated to produce additional recyclable feed.

The remainder of the hydroalkylation reaction effluent, composed mainly of (methylcyclohexyl)toluenes, is then dehydrogenated to convert the (methylcyclohexyl)toluenes to the corresponding methyl-substituted biphenyl compounds. The dehydrogenation is conveniently conducted at a temperature from about 200° C. to about 600° C. and a pressure from about 100 kPa to about 3550 kPa (atmospheric to about 500 psig) in the presence of dehydrogenation catalyst. A suitable dehydrogenation catalyst comprises one or more elements or compounds thereof selected from Group 10 of the Periodic Table of Elements, for example platinum and/or palladium, on a support, such as silica, alumina or carbon nanotubes. In one embodiment, the Group 10 element (such as platinum) is present in amount from 0.1 to 5 wt % of the catalyst. In some cases, the dehydrogenation catalyst may also include tin or a tin compound to improve the selectivity to the desired methyl-substituted biphenyl product. In one embodiment, the tin is present in an amount from 0.05 to 2.5 wt % of the catalyst.

The product of the dehydrogenation reaction comprises a mixture of dimethylbiphenyl isomers together with co-produced hydrogen, and up to 90 wt %, more typically from 0 to 30 wt %, residual (methylcyclohexyl)toluenes. In addition, the dehydrogenation product may contain residual toluene, as well as by-products, such as methylcyclohexane, dimethylcyclohexylbenzene, and $C_{15}+$ heavy hydrocarbons in addition to the target dimethylbiphenyl isomers. Thus, in some embodiments, prior to any separation of the dimethylbiphenyl isomers, the raw dehydrogenation product is subjected to a rough cut separation to remove at least part of the residues and by-products with significantly different boiling points from the dimethylbiphenyl isomers. For example, the hydrogen by-product can be removed and recycled to the hydroalkylation and/or dehydrogenation steps, while residual toluene and methylcyclohexane by-product can be removed and recycled to the hydroalkylation step. Similarly, part of the heavy ($C_{15}+$) components can be removed in the rough cut separation and can be recovered for use as a fuel or can be reacted with toluene over a transalkylation catalyst to convert some of the dialkylate to additional (methylcyclohexyl)toluene. A suitable rough cut separation can be achieved by distillation. For example, the $H_2$ and $C_7$ components can be stripped from the $C_{12+}$ components without reflux.

After partial removal of the by-products and residual components in the rough cut separation, the remaining dehydrogenation product is subjected to one or more DMPB separation steps, in which the product is separated into at least a first stream rich in one or more of the 3,3', 3,4' and 4,4' dimethylbiphenyl isomers and at least one second stream comprising one or more 2,X' (where X' is 2', 3', or 4') dimethylbiphenyl isomers. The second stream will also typically contain most of the unreacted MCHT and most of the dimethylcyclohexylbenzene by-product in the raw dimethylbiphenyl product. The second stream may also contain some or all of the 3,3' dimethylbiphenyl isomer present in the dehydrogenation product. Suitable processes for effecting the DMPB separation include fractional crystallization and/or distillation operating below or, more preferably at, atmospheric pressure.

Part or all of the 2,X'-dimethylbiphenyl (DMPB) isomers in the second stream described above, either alone or together with part or all 3,3' dimethylbiphenyl present in the second stream, is then fed (recycled) to the isomerization process of the present invention, where the DMPB composition of the feed is returned toward equilibrium distribution thereby increasing the concentration of 3,4' and 4,4' dimethylbiphenyl (DMPB) in the feed.

In a further embodiment, the DMPB feed to the present isomerization process is derived from benzene by initially converting the benzene to biphenyl. For example, benzene can be converted directly to biphenyl by reaction with oxygen over an oxidative coupling catalyst as follows:

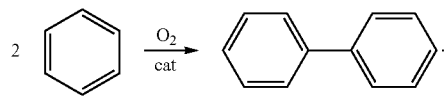

Details of the oxidative coupling of benzene can be found in Ukhopadhyay, Sudip; Rothenberg, Gadi; Gitis, Diana; Sasson, Yoel, Casali Institute of Applied Chemistry, Hebrew University of Jerusalem, Israel, *Journal of Organic Chemistry* (2000), 65(10), pp. 3107-3110, incorporated herein by reference.

Alternatively, benzene can be converted to biphenyl by hydroalkylation to cyclohexylbenzene according to the reaction:

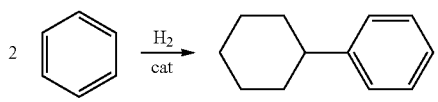

followed by dehydrogenation of the cyclohexylbenzene as follows:

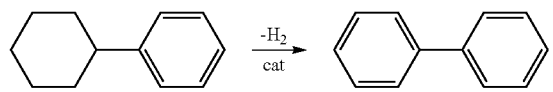

In such a process, the benzene hydroalkylation can be conducted in the same manner as described above for the hydroalkylation of toluene, while the dehydrogenation of the cyclohexylbenzene can be conducted in the same manner as described above for the dehydrogenation of (methylcyclohexyl)toluene.

In either case, the biphenyl product of the oxidative coupling step or the hydroalkylation/dehydrogenation sequence is then methylated, for example with methanol, to produce dimethylbiphenyl. Any known alkylation catalyst can be used for the methylation reaction, such as an intermediate pore molecular sieve having a Constraint Index (as defined in U.S. Pat. No. 4,016,218) of 3 to 12, for example ZSM-5.

The composition of the methylated product will depend on the catalyst and conditions employed in the methylation reaction, but inevitably will comprise a mixture of the different isomers of dimethylbiphenyl at or near the equilibrium distribution shown in FIG. 1. Thus, as with the dehydrogenation product of the toluene-derived feed disclosed above, the methylated product is initially subjected to one or more separation steps to recover part or all of the 3,3', 3,4' and 4,4' dimethylbiphenyl isomers, before the remaining 2,X' DMPB enriched fraction is supplied to the isomerization process of the present invention.

Irrespective of the method used to produce the DMPB isomer mixture employed herein, it is to be appreciated that the isomerization process of the invention can be used to convert part or all of the 3,3', 3,4' and 4,4' isomer components, in addition to the 2,X' isomer components, of the DMPB feed. Thus, for example, in one embodiment the DMPB feed may be initially separated into a first fraction comprising one or more 3,3', 3,4' and 4,4' dimethylbiphenyl isomers and a second fraction comprising one or more 2,X' dimethylbiphenyl isomers. The first fraction is then further separated into a third fraction enriched in one target isomer selected from 3,3', 3,4' and 4,4' dimethylbiphenyl and a fourth fraction depleted in the target isomer. The second and fourth fractions can then be supplied to separate or the same isomerization reactor where the relevant fraction(s) are contacted with a solid acid catalyst under isomerization conditions.

In another embodiment, this invention relates to:
1. A process for converting at least one isomer of a dialkyl-substituted biphenyl compound into at least one different isomer, the process comprising contacting a feed comprising the dialkyl-substituted biphenyl compound isomer with an acid catalyst under isomerization conditions.
2. The process of paragraph 1, wherein the isomerization conditions comprise a temperature from 100° C. to 450° C. and a pressure from 2 to 7,000 kPa.
3. The process of paragraph 1 or paragraph 2, wherein the contacting is conducted in the presence of a solid acid catalyst, preferably a molecular sieve catalyst, more preferably a molecular sieve selected from the group consisting of BEA, FAU and MOR structure type molecular sieves and mixtures thereof.
4. The process of any one of paragraphs 1 to 3, wherein the dialkyl-substituted biphenyl compound comprises dimethylbiphenyl.
5. A process for producing 3,3', 3,4' and/or 4,4' dialkylbiphenyl compounds, the process comprising:
    (a1) contacting a feed comprising one or more 2,X' dialkylbiphenyl isomers (where X' is 2', 3' and/or 4') with an acid catalyst under isomerization conditions effective to convert at least some of the 2,X' dialkylbiphenyl isomers into one or more 3,3', 3,4' and 4,4' dialkylbiphenyl isomers and produce an isomerization effluent.
6. The process of paragraph 5, wherein the contacting (a1) is conducted at a temperature from 100° C. to 450° C. and a pressure from 2 to 7,000 kPa.
7. The process of paragraph 5 or paragraph 6, wherein the contacting (a1) is conducted in the presence of a solid acid catalyst, preferably a molecular sieve catalyst, more preferably a molecular sieve selected from the group consisting of BEA, FAU and MOR structure type molecular sieves and mixtures thereof.
8. The process of any one of paragraphs 5 to 7 and further comprising:
    (b1) supplying at least part of the isomerization effluent to a separation zone to recover one or more of the 3,3', 3,4' and 4,4' dialkylbiphenyl isomers in the isomerization effluent and produce a residual fraction enriched in one or more of the 2,X' dialkylbiphenyl isomers as compared with the isomerization effluent; and
    (c1) recycling at least part of the residual fraction to the contacting (a1).
9. The process of any one of paragraphs 5 to 8, wherein the dialkylbiphenyl isomers comprise dimethylbiphenyl isomers.
10. The process of any one of paragraphs 5 to 9 and further comprising:
    (d1) contacting toluene with hydrogen in the presence of a hydroalkylation catalyst under conditions effective to produce a hydroalkylation product comprising (methylcyclohexyl)toluenes;
    (e1) dehydrogenating at least part of the hydroalkylation product under conditions effective to produce a dehydrogenation product comprising dimethylbiphenyl isomers and unreacted (methylcyclohexyl)toluenes;
    (f1) supplying at least part of the dehydrogenation product to a separation zone to recover a first fraction enriched in one or more 3,3', 3,4' and/or 4,4' dimethylbiphenyl isomers as compared with the dehydrogenation product and a second fraction enriched in one or more of 2,X' dimethylbiphenyl isomers as compared with the dehydrogenation product and also containing at least part of the unreacted (methylcyclohexyl)toluenes; and
    (g1) supplying at least part of the second fraction as at least part of the feed to the contacting (a1).
11. The process of paragraph 10, wherein the hydroalkylation catalyst comprises an acidic component and a hydrogenation component.
12. The process of paragraph 11, wherein the acidic component of the hydroalkylation catalyst comprises a molecular sieve, preferably a molecular sieve selected from the group consisting of BEA and FAU structure type molecular sieves, molecular sieves of the MCM-22 family and mixtures thereof.

13. The process of paragraph 11 or paragraph 12, wherein the hydrogenation component of the hydroalkylation catalyst is selected from the group consisting of palladium, ruthenium, nickel, zinc, tin, cobalt, silver, gold, platinum and compounds and mixtures thereof.

14. The process of any one of paragraphs 10 to 13, wherein the conditions in the contacting (d1) include a temperature from 100° C. to 400° C., a pressure from 10 to 7,000 kPa and a molar ratio of hydrogen to toluene supplied to the contacting (d1) from 0.15:1 to 15:1.

15. The process of paragraph 9 and further comprising:
 (h1) contacting biphenyl with a methylating agent in the presence of an alkylation catalyst under conditions effective to produce a methylation reaction product comprising a mixture of dimethyl-substituted biphenyl isomers;
 (i1) supplying at least part of the methylation reaction product to a separation zone to recover a first fraction enriched in one or more 3,3', 3,4' and 4,4' dimethylbiphenyl isomers as compared with the methylation reaction product and a second fraction enriched in one or more of 2,X' dimethylbiphenyl isomers as compared with the methylation reaction product; and
 (g1) supplying at least part of the second fraction as at least part of the feed to the contacting (a1).

16. The process of paragraph 15, wherein the biphenyl is produced by oxidative coupling of benzene.

17. The process of paragraph 15, wherein the biphenyl is produced by hydroalkylation of benzene to cyclohexylbenzene followed by dehydrogenation of the cyclohexylbenzene.

18. A process for producing 3,3', 3,4' and/or 4,4' dimethylbiphenyl compounds, the process comprising:
 (a2) contacting toluene with hydrogen in the presence of a hydroalkylation catalyst under conditions effective to produce a hydroalkylation product comprising (methylcyclohexyl)toluenes;
 (b2) dehydrogenating at least part of the hydroalkylation product under conditions effective to produce a dehydrogenation product comprising dimethylbiphenyl isomers and unreacted (methylcyclohexyl)toluenes;
 (c2) separating the dehydrogenation product into a first fraction comprising one or more 3,3', 3,4' and 4,4' dimethylbiphenyl isomers and a second fraction comprising one or more 2,X' dimethylbiphenyl isomers (where X' is 2, 3 or 4) and at least part of the unreacted (methylcyclohexyl)toluenes;
 (d2) contacting at least part of the second fraction with an acid catalyst under isomerization conditions effective to convert at least some of the 2,X' dimethylbiphenyl isomers into one or more 3,3', 3,4' and 4,4' dimethylbiphenyl isomers and produce an isomerization product; and
 (e2) recycling at least part of the isomerization product to the separating (c2).

19. The process of paragraph 18, wherein the hydroalkylation catalyst comprises an acidic component and a hydrogenation component.

20. The process of paragraph 19, wherein the acidic component of the hydroalkylation catalyst comprises a molecular sieve, preferably a molecular sieve selected from the group consisting of BEA and FAU structure type molecular sieves, molecular sieves of the MCM-22 family and mixtures thereof.

21. The process of paragraph 19 or paragraph 20, wherein the hydrogenation component of the hydroalkylation catalyst is selected from the group consisting of palladium, ruthenium, nickel, zinc, tin, cobalt, silver, gold, platinum and compounds and mixtures thereof.

22. The process of any one of paragraphs 18 to 21, wherein the conditions in the contacting (a2) include a temperature from 100° C. to 400° C., a pressure from 10 to 7,000 kPa and a molar ratio of hydrogen to toluene supplied to the contacting (a2) from 0.15:1 to 15:1.

23. The process of any one of paragraphs 18 to 22, wherein the contacting (d2) is conducted at a temperature from 100° C. to 450° C. and a pressure from 10 to 7,000 kPa.

24. The process of any one of paragraphs 18 to 23, wherein the contacting (d2) is conducted in the presence of a solid acid catalyst, preferably a molecular sieve catalyst selected from the group consisting of BEA, FAU and MOR structure type molecular sieves and mixtures thereof.

25. The process of any one of paragraphs 18 to 24 and further comprising:
 (f2) separating the first fraction into a third fraction enriched in one target isomer selected from 3,3', 3,4' and 4,4' dimethylbiphenyl and a fourth fraction depleted in said target isomer;
 (g2) contacting at least part of the fourth fraction with an acid catalyst under isomerization conditions effective to produce an isomerization product having an increased concentration of the target isomer as compared with the fourth fraction; and
 (h2) recycling at least part of the isomerization product to the separating (f2).

26. A process for producing 3,3', 3,4' and/or 4,4' dimethylbiphenyl compounds, the process comprising:
 (a3) contacting toluene with hydrogen in the presence of a hydroalkylation catalyst under conditions effective to produce a hydroalkylation product comprising (methylcyclohexyl)toluenes;
 (b3) dehydrogenating at least part of the hydroalkylation product under conditions effective to produce a dehydrogenation product comprising dimethylbiphenyl isomers and unreacted (methylcyclohexyl)toluenes;
 (c3) supplying at least part of the dehydrogenation product to a separation zone to recover a first fraction enriched in one or more 3,3', 3,4' and/or 4,4' dimethylbiphenyl isomers as compared with the dehydrogenation product and a second fraction enriched in one or more of 2,X' dimethylbiphenyl isomers (where X' is 2', 3' and/or 4') as compared with the dehydrogenation product and also containing at least part of the unreacted (methylcyclohexyl)toluenes; and
 (d3) supplying at least part of the second fraction as at least part of a feed to an isomerization process comprising contacting the feed comprising one or more 2,X' dimethylbiphenyl isomers with an acid catalyst under isomerization conditions effective to convert at least some of the 2,X' dimethylbiphenyl isomers into one or more 3,3', 3,4' and 4,4' dimethylbiphenyl isomers and produce an isomerization effluent.

27. A process for producing 3,3', 3,4' and/or 4,4' dimethylbiphenyl compounds, the process comprising:
 (a4) contacting biphenyl with a methylating agent in the presence of an alkylation catalyst under conditions effective to produce a methylation reaction product comprising a mixture of dimethyl-substituted biphenyl isomers;
 (b4) supplying at least part of the methylation reaction product to a separation zone to recover a first fraction enriched in one or more 3,3', 3,4' and 4,4' dimethylbiphenyl isomers as compared with the methylation reaction product and a second fraction enriched in one or more of 2,X' dimethylbiphenyl isomers (where X' is 2', 3' and/or 4') as compared with the methylation reaction product; and (c4) supplying at least part of the second fraction as at least part of a feed to an isomerization process comprising contacting the feed comprising one or more 2,X' dimethylbiphenyl isomers with an acid catalyst under isomerization conditions effective to convert at least some of the 2,X' dimethylbiphenyl isomers into one or more 3,3', 3,4' and 4,4' dimethylbiphenyl isomers and produce an isomerization effluent.

28. A process for producing 3,3', 3,4' and/or 4,4' dimethylbiphenyl compounds, the process comprising:

(a5) contacting toluene with hydrogen in the presence of a hydroalkylation catalyst under conditions effective to produce a hydroalkylation product comprising (methylcyclohexyl)toluenes;

(b5) dehydrogenating at least part of the hydroalkylation product under conditions effective to produce a dehydrogenation product comprising dimethylbiphenyl isomers and unreacted (methylcyclohexyl)toluenes;

(c5) separating the dehydrogenation product into a first fraction comprising one or more 3,3', 3,4' and 4,4' dimethylbiphenyl isomers and a second fraction comprising one or more 2,X' dimethylbiphenyl isomers (where X' is 2, 3 or 4) and at least part of the unreacted (methylcyclohexyl)toluenes;

(d5) contacting at least part of the second fraction with an acid catalyst under isomerization conditions effective to convert at least some of the 2,X' dimethylbiphenyl isomers into one or more 3,3', 3,4' and 4,4' dimethylbiphenyl isomers and produce an isomerization product;

(e5) recycling at least part of the isomerization product to the separating (c5); and (f5) optionally, separating the first fraction into a third fraction enriched in one target isomer selected from 3,3', 3,4' and 4,4' dimethylbiphenyl and a fourth fraction depleted in said target isomer;

(g5) contacting at least part of the fourth fraction with an acid catalyst under isomerization conditions effective to produce an isomerization product having an increased concentration of the target isomer as compared with the fourth fraction; and (h5) recycling at least part of the isomerization product to the separating (f5).

This invention further relates to:

1A. A process for converting at least one isomer of a dialkyl-substituted biphenyl compound into at least one different isomer, the process comprising contacting a feed comprising the dialkyl-substituted biphenyl compound isomer with an acid catalyst under isomerization conditions.

2A. The process of paragraph 1A, wherein the isomerization conditions comprise a temperature from 100° C. to 450° C. and a pressure from 2 to 7,000 kPa.

3A. The process of paragraph 1A, wherein the contacting is conducted in the presence of a solid acid catalyst.

4A. The process of paragraph 1A, wherein the contacting is conducted in the presence of a molecular sieve catalyst.

5A. The process of paragraph 1A, wherein the contacting is conducted in the presence of a molecular sieve selected from the group consisting of BEA, FAU and MOR structure type molecular sieves and mixtures thereof.

6A. The process of paragraph 1A, wherein the dialkyl-substituted biphenyl compound comprises dimethylbiphenyl.

7A. A process for producing 3,3', 3,4' and/or 4,4' dialkylbiphenyl compounds, the process comprising:

(a1) contacting a feed comprising one or more 2,X' dialkylbiphenyl isomers (where X' is 2', 3' and/or 4') with an acid catalyst under isomerization conditions effective to convert at least some of the 2,X' dialkylbiphenyl isomers into one or more 3,3', 3,4' and 4,4' dialkylbiphenyl isomers and produce an isomerization effluent.

8A. The process of paragraph 7A, wherein the contacting (a1) is conducted at a temperature from 100° C. to 450° C. and a pressure from 2 to 7,000 kPa.

9A. The process of paragraph 7A, wherein the contacting (a1) is conducted in the presence of a solid acid catalyst.

10A. The process of paragraph 1A, wherein the contacting (a1) is conducted in the presence of a molecular sieve catalyst.

11A. The process of paragraph 7A, wherein the contacting (a1) is conducted in the presence of a molecular sieve selected from the group consisting of BEA, FAU and MOR structure type molecular sieves and mixtures thereof.

12A. The process of paragraph 7A and further comprising:

(b1) supplying at least part of the isomerization effluent to a separation zone to recover one or more of the 3,3', 3,4' and 4,4' dialkylbiphenyl isomers in the isomerization effluent and produce a residual fraction enriched in one or more of the 2,X' dialkylbiphenyl isomers as compared with the isomerization effluent; and (c1) recycling at least part of the residual fraction to the contacting (a1).

13A. The process of paragraph 7A, wherein the dialkylbiphenyl isomers comprise dimethylbiphenyl isomers.

14A. The process of paragraph 13A and further comprising:

(d1) contacting toluene with hydrogen in the presence of a hydroalkylation catalyst under conditions effective to produce a hydroalkylation product comprising (methylcyclohexyl)toluenes;

(e1) dehydrogenating at least part of the hydroalkylation product under conditions effective to produce a dehydrogenation product comprising dimethylbiphenyl isomers and unreacted (methylcyclohexyl)toluenes;

(f1) supplying at least part of the dehydrogenation product to a separation zone to recover a first fraction enriched in one or more 3,3', 3,4' and/or 4,4' dimethylbiphenyl isomers as compared with the dehydrogenation product and a second fraction enriched in one or more of 2,X' dimethylbiphenyl isomers as compared with the dehydrogenation product and also containing at least part of the unreacted (methylcyclohexyl)toluenes; and (g1) supplying at least part of the second fraction as at least part of the feed to the contacting (a1).

15A. The process of paragraph 14A, wherein the hydroalkylation catalyst comprises an acidic component and a hydrogenation component.

16A. The process of paragraph 15A, wherein the acidic component of the hydroalkylation catalyst comprises a molecular sieve.

17A. The process of paragraph 14A, wherein the hydroalkylation catalyst comprises a molecular sieve selected from the group consisting of BEA and FAU structure type molecular sieves, molecular sieves of the MCM-22 family and mixtures thereof.

18A. The process of paragraph 14A, wherein the hydroalkylation catalyst comprises a molecular sieve of the MCM-22 family.

19A. The process of paragraph 15A, wherein the hydrogenation component of the hydroalkylation catalyst is selected from the group consisting of palladium, ruthenium, nickel, zinc, tin, cobalt, silver, gold, platinum and compounds and mixtures thereof.

20A. The process of paragraph 14A, wherein the conditions in the contacting (d1) include a temperature from 100° C. to 400° C. and a pressure from 10 to 7,000 kPa.

21A. The process of paragraph 14A, wherein the molar ratio of hydrogen to toluene supplied to the contacting (d1) is from 0.15:1 to 15:1.

22A. The process of paragraph 13 and further comprising:
- (h1) contacting biphenyl with a methylating agent in the presence of an alkylation catalyst under conditions effective to produce a methylation reaction product comprising a mixture of dimethyl-substituted biphenyl isomers;
- (i1) supplying at least part of the methylation reaction product to a separation zone to recover a first fraction enriched in one or more 3,3', 3,4' and 4,4' dimethylbiphenyl isomers as compared with the methylation reaction product and a second fraction enriched in one or more of 2,X' dimethylbiphenyl isomers as compared with the methylation reaction product; and
- (g1) supplying at least part of the second fraction as at least part of the feed to the contacting (a1).

23A. The process of paragraph 22A, wherein the biphenyl is produced by oxidative coupling of benzene.

24A. The process of paragraph 22A, wherein the biphenyl is produced by hydroalkylation of benzene to cyclohexylbenzene followed dehydrogenation of the cyclohexylbenzene.

25A. A process for producing 3,3', 3,4' and/or 4,4' dimethylbiphenyl compounds, the process comprising:
- (a2) contacting toluene with hydrogen in the presence of a hydroalkylation catalyst under conditions effective to produce a hydroalkylation product comprising (methylcyclohexyl)toluenes;
- (b2) dehydrogenating at least part of the hydroalkylation product under conditions effective to produce a dehydrogenation product comprising dimethylbiphenyl isomers and unreacted (methylcyclohexyl)toluenes;
- (c2) separating the dehydrogenation product into a first fraction comprising one or more 3,3', 3,4' and 4,4' dimethylbiphenyl isomers and a second fraction comprising one or more 2,X' dimethylbiphenyl isomers (where X' is 2, 3 or 4) and at least part of the unreacted (methylcyclohexyl)toluenes;
- (d2) contacting at least part of the second fraction with an acid catalyst under isomerization conditions effective to convert at least some of the 2,X' dimethylbiphenyl isomers into one or more 3,3', 3,4' and 4,4' dimethylbiphenyl isomers and produce an isomerization product; and
- (e2) recycling at least part of the isomerization product to the separating (c2).

26A. The process of paragraph 25A, wherein the hydroalkylation catalyst comprises an acidic component and a hydrogenation component.

27A. The process of paragraph 26A, wherein the acidic component of the hydroalkylation catalyst comprises a molecular sieve.

28A. The process of paragraph 26A, wherein the hydroalkylation catalyst comprises a molecular sieve selected from the group consisting of BEA and FAU structure type molecular sieves, molecular sieves of the MCM-22 family and mixtures thereof.

29A. The process of paragraph 26A, wherein the hydroalkylation catalyst comprises a molecular sieve of the MCM-22 family.

30A. The process of paragraph 26A, wherein the hydrogenation component of the hydroalkylation catalyst is selected from the group consisting of palladium, ruthenium, nickel, zinc, tin, cobalt, silver, gold, platinum and compounds and mixtures thereof.

31A. The process of paragraph 25A, wherein the conditions in the contacting (a2) include a temperature from 100° C. to 400° C. and a pressure from 10 to 7,000 kPa.

32A. The process of paragraph 25A, wherein the molar ratio of hydrogen to toluene supplied to the contacting (a2) is from 0.15:1 to 15:1.

33A. The process of paragraph 25A, wherein the contacting (d2) is conducted at a temperature from 100° C. to 450° C. and a pressure from 10 to 7,000 kPa.

34A. The process of paragraph 25A, wherein the contacting (d2) is conducted in the presence of a solid acid catalyst.

35A. The process of paragraph 25A, wherein the contacting (d2) is conducted in the presence of a molecular sieve catalyst selected from the group consisting of BEA, FAU and MOR structure type molecular sieves and mixtures thereof.

36A. The process of paragraph 25A and further comprising:
- (f2) separating the first fraction into a third fraction enriched in one target isomer selected from 3,3', 3,4' and 4,4' dimethylbiphenyl and a fourth fraction depleted in said target isomer;
- (g2) contacting at least part of the fourth fraction with an acid catalyst under isomerization conditions effective to produce an isomerization product having an increased concentration of the target isomer as compared with the fourth fraction; and
- (h2) recycling at least part of the isomerization product to the separating (f2).

37A. A process for producing 3,3', 3,4' and/or 4,4' dimethylbiphenyl compounds, the process comprising:
- (a3) contacting toluene with hydrogen in the presence of a hydroalkylation catalyst under conditions effective to produce a hydroalkylation product comprising (methylcyclohexyl)toluenes;
- (b3) dehydrogenating at least part of the hydroalkylation product under conditions effective to produce a dehydrogenation product comprising dimethylbiphenyl isomers and unreacted (methylcyclohexyl)toluenes;
- (c3) supplying at least part of the dehydrogenation product to a separation zone to recover a first fraction enriched in one or more 3,3', 3,4' and/or 4,4' dimethylbiphenyl isomers as compared with the dehydrogenation product and a second fraction enriched in one or more of 2,X' dimethylbiphenyl isomers (where X' is 2', 3' and/or 4') as compared with the dehydrogenation product and also containing at least part of the unreacted (methylcyclohexyl)toluenes; and
- (d3) supplying at least part of the second fraction as at least part of a feed to an isomerization process comprising contacting the feed comprising one or more 2,X' dimethylbiphenyl isomers with an acid catalyst under isomerization conditions effective to convert at least some of the 2,X' dimethylbiphenyl isomers into one or more 3,3', 3,4' and 4,4' dimethylbiphenyl isomers and produce an isomerization effluent.

38A. A process for producing 3,3', 3,4' and/or 4,4' dimethylbiphenyl compounds, the process comprising:
- (a4) contacting biphenyl with a methylating agent in the presence of an alkylation catalyst under conditions effective to produce a methylation reaction product comprising a mixture of dimethyl-substituted biphenyl isomers;
- (b4) supplying at least part of the methylation reaction product to a separation zone to recover a first fraction enriched in one or more 3,3', 3,4' and 4,4' dimethylbiphenyl isomers as compared with the methylation reaction product and a second fraction enriched in one or more of 2,X' dimethylbiphenyl isomers (where X' is 2', 3' and/or 4') as compared with the methylation reaction product; and
- (c4) supplying at least part of the second fraction as at least part of a feed to an isomerization process comprising contacting the feed comprising one or more 2,X' dimethylbiphenyl isomers with an acid catalyst under isomerization conditions effective to convert at least some of the 2,X' dimethylbiphenyl isomers into one or more 3,3', 3,4' and 4,4' dimethylbiphenyl isomers and produce an isomerization effluent.

39A. A process for producing 3,3', 3,4' and/or 4,4' dimethylbiphenyl compounds, the process comprising:
- (a5) contacting toluene with hydrogen in the presence of a hydroalkylation catalyst under conditions effective to produce a hydroalkylation product comprising (methylcyclohexyl)toluenes;
- (b5) dehydrogenating at least part of the hydroalkylation product under conditions effective to produce a dehydrogenation product comprising dimethylbiphenyl isomers and unreacted (methylcyclohexyl)toluenes;
- (c5) separating the dehydrogenation product into a first fraction comprising one or more 3,3', 3,4' and 4,4' dimethylbiphenyl isomers and a second fraction comprising one or more 2,X' dimethylbiphenyl isomers (where X' is 2, 3 or 4) and at least part of the unreacted (methylcyclohexyl)toluenes;
- (d5) contacting at least part of the second fraction with an acid catalyst under isomerization conditions effective to convert at least some of the 2,X' dimethylbiphenyl isomers into one or more 3,3', 3,4' and 4,4' dimethylbiphenyl isomers and produce an isomerization product;
- (e5) recycling at least part of the isomerization product to the separating (c5);
- (f5) optionally, separating the first fraction into a third fraction enriched in one target isomer selected from 3,3', 3,4' and 4,4' dimethylbiphenyl and a fourth fraction depleted in said target isomer;
- (g5) contacting at least part of the fourth fraction with an acid catalyst under isomerization conditions effective to produce an isomerization product having an increased concentration of the target isomer as compared with the fourth fraction; and
- (h5) recycling at least part of the isomerization product to the separating (f5).

The invention will now be more particularly described with reference to the following non-limiting Examples and FIGS. 2 to 8 of the accompanying drawings.

In the Examples, samples were analyzed on an Agilent 7890 Gas Chromatograph equipped with FID detector and an automatic liquid sampler (ALS). Typical injection size was about 0.2 μl. The columns used were from Supelco of the Dex type. A Gamma Dex column was joined together with a Beta Dex column to give a total length of 120 m (60 m for each type). The internal diameter of the columns was 0.25 mm. The GC was operated in constant flow mode with an initial pressure of about 78 psi and column flow of about 3.0 ml/min using helium as carrier gas. The following oven procedure was used:

Initial temperature of 140° C., hold for 30 minutes;
Ramp 1 at 2° C./min to 180° C., hold for 20 minutes;
Ramp 2 at 3° C./min to 220° C., hold for 7 minutes; and
Total analysis time of 90.33 minutes.

Examples 1 to 13: Study of Dimethylbiphenyl Isomerization in Batch Reactor

A study of 12 different catalysts for the isomerization of 2,X' dimethylbiphenyl was conducted in a mini reactor in a furnace. The catalysts employed are shown in Table 2.

TABLE 2

| Example | Catalyst |
|---|---|
| 1 | 65 wt % MCM-22, 35 wt % $Al_2O_3$ |
| 2 | 80 wt % MCM-49, 20 wt % $Al_2O_3$ |
| 3 | 80 wt % Beta, 20 wt % $Al_2O_3$ |
| 4 | 60 wt % MCM-56, 40 wt % $Al_2O_3$ |
| 5 | 2.5 wt % Mg on 65 wt % TEA mordenite, 35 wt % $Al_2O_3$ |
| 6 | ZSM-12 crystal |
| 7 | MCM-49 crystal |
| 8 | 2.7 wt % Mo on MCM-49 crystal |
| 9 | 65 wt % TEA mordenite, 35 wt % $Al_2O_3$ |
| 10 | 50 wt % ZSM-5, 50 wt % $Al_2O_3$ |
| 11 | 1.8 wt % $B_2O_3$ on $Al_2O_3$ |
| 12 | 65 wt % ZSM-12, 35 wt % $SiO_2$ |
| 13 | 80% USY, 20% $Al_2O_3$ |

The catalyst of Example 11 was prepared by incipient wetness impregnation of RT-225 $Al_2O_3$ extrudates with surface area of 306 $m^2/g$, pore volume of 0.85 $cm^3/g$, and pore size of 73 Å with boric acid. For example, 1.6554 g of boric acid $H_3BO_3$ was dissolved in 25 g of water. The boric acid solution volume was adjusted to 43.2 ml with water, which was about 95% of the water absorption capacity of 50 g of the $Al_2O_3$. After impregnation, the boron containing catalyst was dried at 250° F. (121° C.) in air for 14 hr. It was then calcined in air at 1000° F. (538° C.) for 4 hrs.

In each experiment, 0.25 g of the catalyst was weighed in the reactor and 2 g of a dimethyl biphenyl (DMBP) mixture (50 wt % 2,3' DMBP+50 wt % 2,4' DMBP) was added to the reactor. The temperature was ramped at 10° C./min to 300° C. and held at 300° C. for 2 hrs, then the reactor was cooled to room temperature at 10° C./min. The furnace was purged with $N_2$. Results are shown in FIG. 2.

Figure 2A:
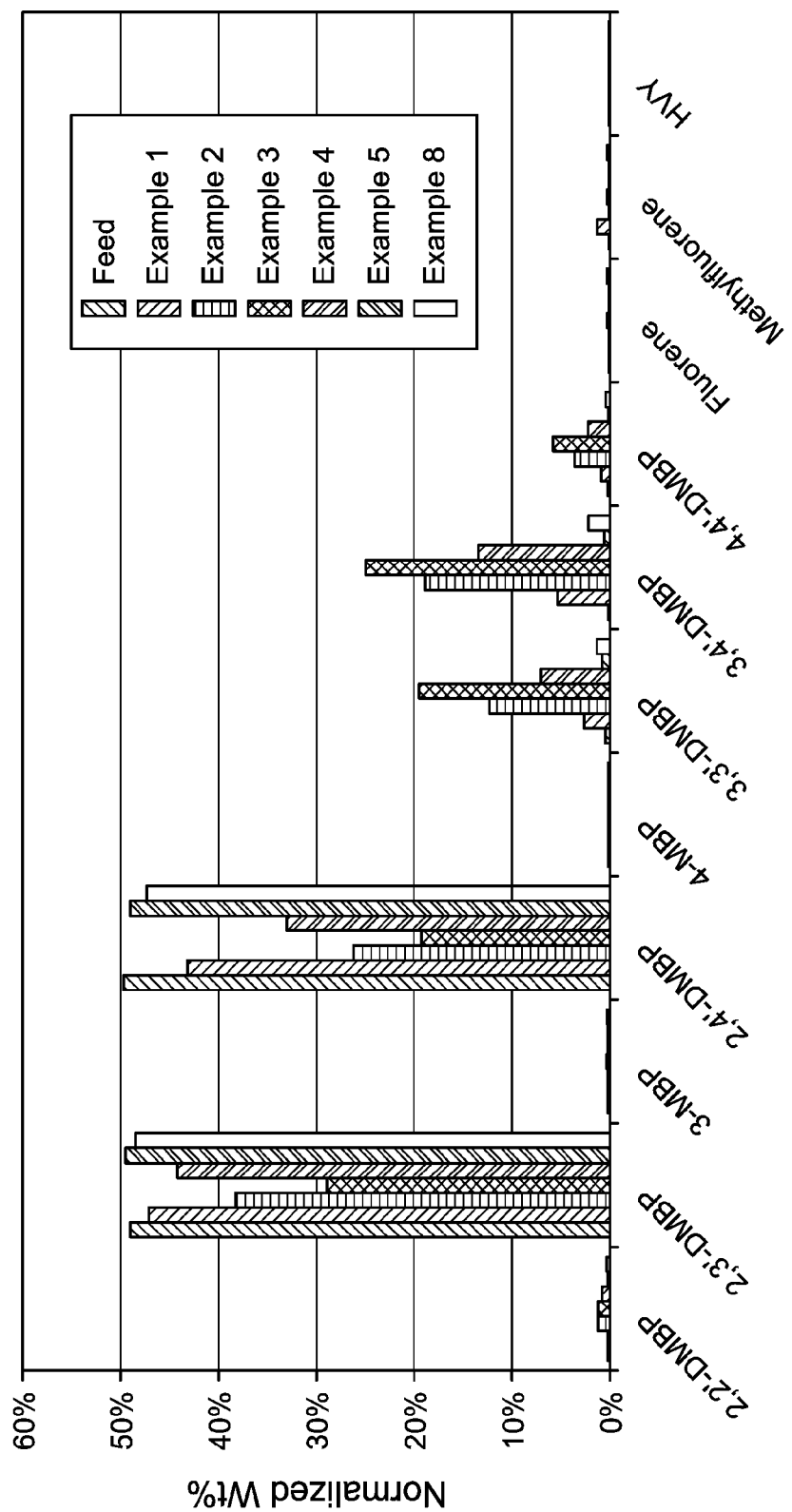
FIGS. 2(a) and (b) are bar graphs comparing the feed and product compositions for the different catalysts used in the DMPB isomerization experiments of Examples 1 to 13.
Figure 2B:
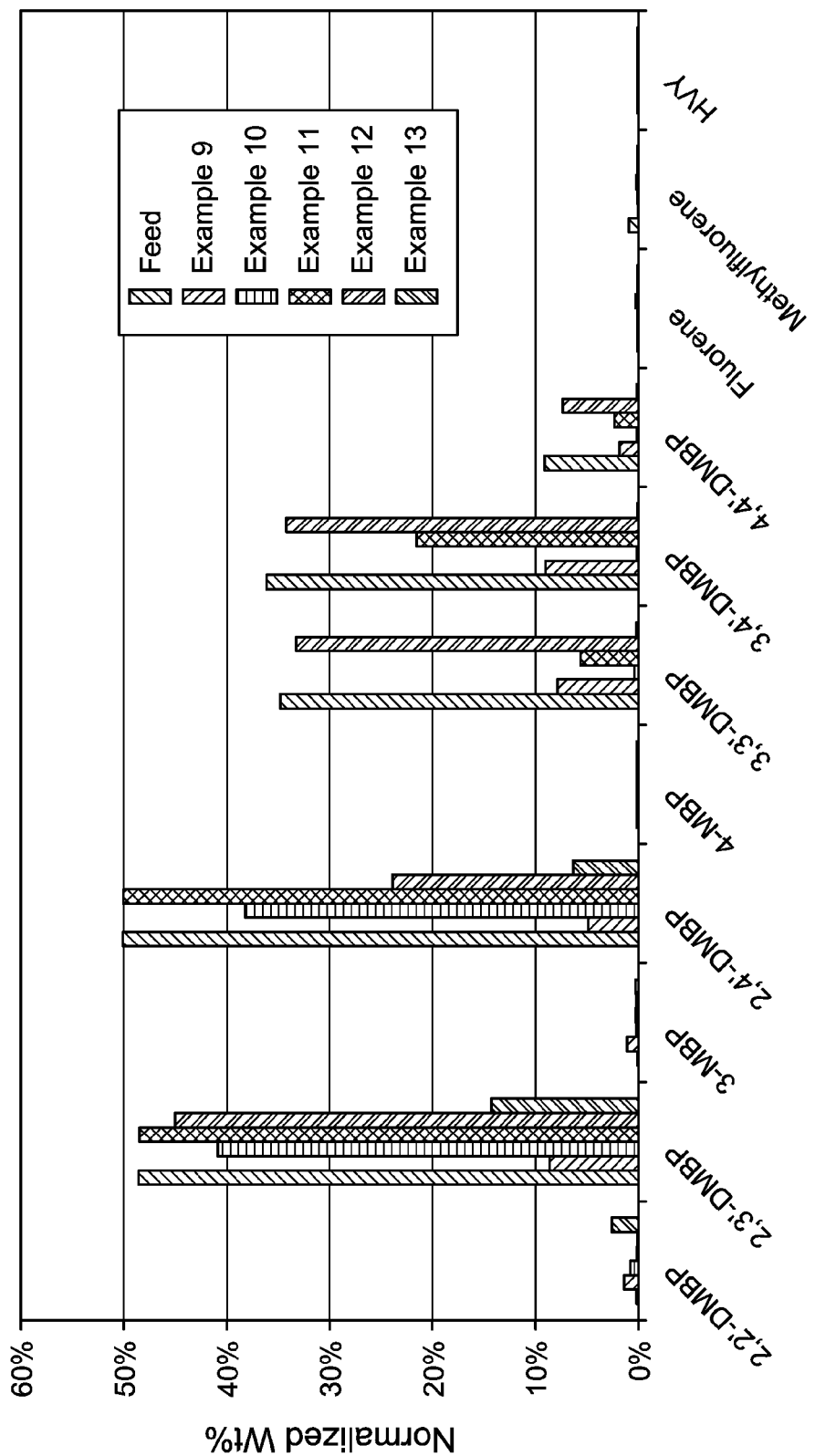

The results shown in FIG. 2 suggest that USY, mordenite (Example 9), and zeolite beta are active for DMBP isomerization. Under these conditions, a net conversion of 81% and 90% was observed over mordenite (Example 9) for 2,3' DMBP and 2,4' DMBP, respectively. The resulting product from the mordenite catalyzed isomerization contained 80% 3,3', 3,4' or 4,4' DMBP isomers (useful isomers for biphenyl based plasticizer applications).

Examples 14 and 15: Study of Dimethylbiphenyl Isomerization in Fixed Bed Reactor In these Examples, isomerization of 2,3' and 2,4' DMBP over the $Al_2O_3$ support of Example 11 (Example 14) and 80 wt % ZSM-5 (25:1 $Si/Al_2$ [mol/mol]), 20 wt % $Al_2O_3$ catalyst (Example 15) were conducted in a continuous, fixed bed reactor.

These experiments utilized a reactor unit with 8 parallel reactors heated by furnace. For different tests anywhere from 1-8 reactors were utilized. The reactors used in these experiments consisted of quartz tubes of 9 mm in diameter. Annular $N_2$ flow on the outside of the quartz reactor allowed for pressure equilibration between the inside and outside of each reactor channel. Catalyst extrudates were crushed to 20/40 mesh loaded in quantities ranging from 0.25-2 g (to vary corresponding weight based space velocity) after being diluted up to 4 g in crushed quartz. A quartz wool plug was used at the top and bottom of the catalyst bed to keep catalyst in place. Two sets of four parallel reactors were placed in heated furnaces to control isothermal reaction temperature. Each reactor contained an internal thermocouple in the catalyst bed in a 1/8" thermowell. The reactors were topped off with the same quartz chips.

An ISCO™ syringe pump was used to introduce the feed to the reactor. The feed was pumped through a vaporizer before being mixed in-line with $H_2$ and/or $N_2$ at a molar ratio of between 0 and 2 (gas to hydrocarbon liquid). The products exiting the reactor were condensed and collected in intervals (1-2 samples per day per reactor) and analyzed offline by GC.

In Examples 14 and 15, 0.5 g of catalyst was loaded in the reactor and the liquid flow rates corresponded to a space velocity of 3 $hr^{-1}$. The liquid feed was a mixture of 35 wt % 2,3' DMBP, 45 wt % 2,4' DMBP and 10 wt % MCHT diluted in 90% toluene. A 1:1 molar co-feed of hydrogen to hydrocarbon was utilized and the reactor pressure was held at 100 psig. Temperatures of 280° C. and 300° C. were tested and the results are shown in FIG. 3.

Figure 3:
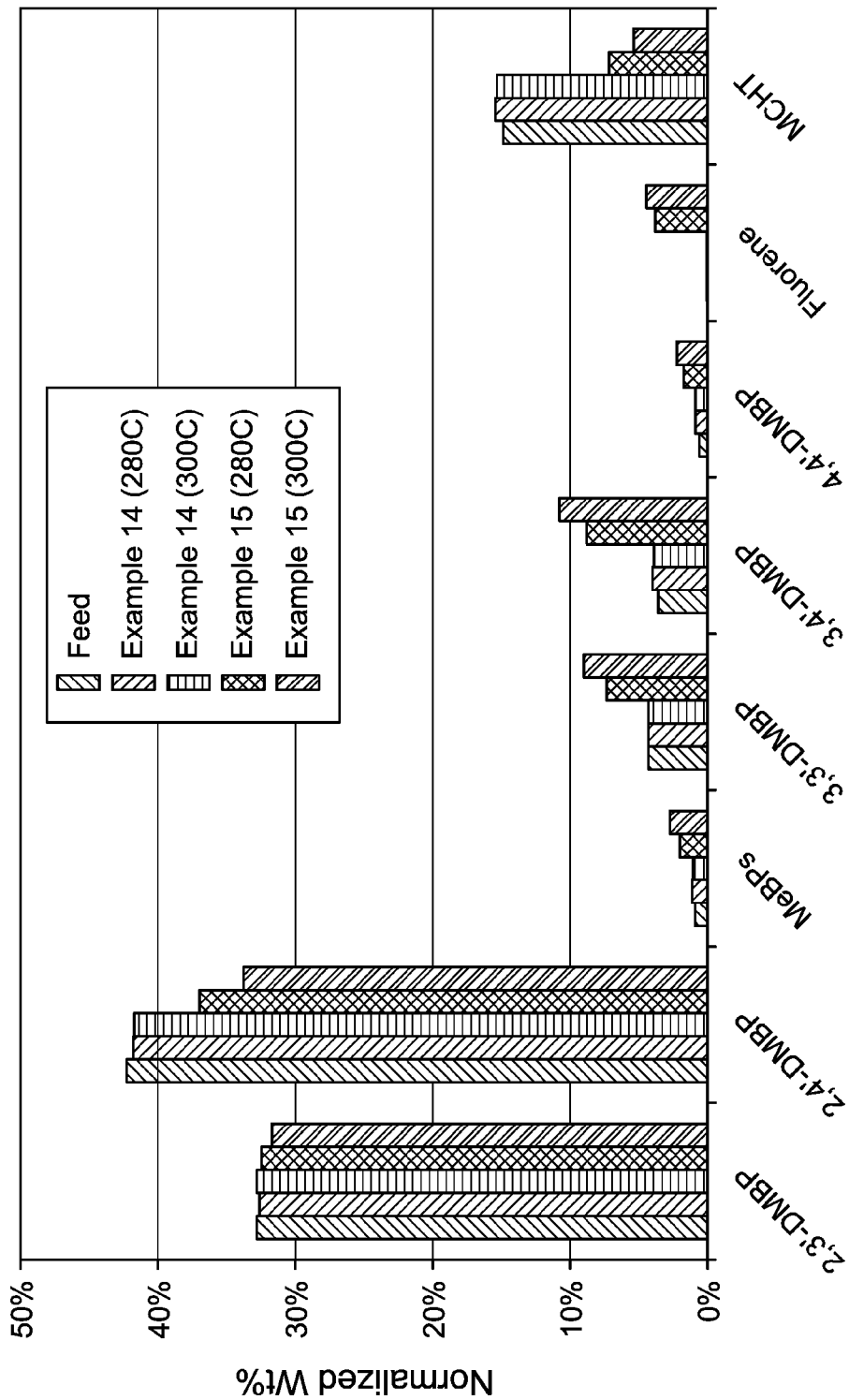
FIG. 3 is a bar graph showing the normalized weight % of >C13 species in the reactor effluent of the DMBP isomerization experiments of Examples 14 and 15.

The data in FIG. 3 illustrate that the ZSM-5 catalyst of Example 15 is superior to the gamma-alumina support of Example 14 in isomerizing DMBP in a fixed bed at the conditions investigated. The results also show that the ZSM-5 catalyst is destructive toward MCHT that was co-fed to the reactor. Lights formation (the result of MCHT cracking) was prevalent over the ZSM-5 catalyst. This underscores the importance of utilizing a catalyst and conditions that are not only active for isomerization, but also are not destructive toward MCHT likely to be present in the isomerization feed.

Examples 16 to 21: Study of Dimethylbiphenyl Isomerization in Fixed Bed Reactor

In these experiments, the fixed bed reactor of Examples 14 and 15 was again employed, with 1 g of catalyst being loaded and liquid flow rates corresponding to a space velocity of 2 $hr^{-1}$. The liquid feed was 2,4' DMBP diluted in 90% toluene. A 0.5:1 molar co-feed of nitrogen was utilized and the reactor pressure was held between 175-180 psig. The catalysts listed in Table 3 were tested:

TABLE 3

| Example | Catalyst |
| --- | --- |
| 16 | 80 wt % ZSM-5 (25:1 Si/$Al_2$), 20 wt % $Al_2O_3$ |
| 17 | 80 wt % USY (60:1 Si/$Al_2$), 20 wt % $Al_2O_3$ |
| 18 | 80 wt % Beta, 20 wt % $Al_2O_3$ |
| 19 | 80 wt % USY (30:1 Si/$Al_2$), 20 wt % $Al_2O_3$ |
| 20 | 65 wt % TEA mordenite (35:1 Si/$Al_2$), 35 wt % $Al_2O_3$ |
| 21 | 65 wt % TEA mordenite (19:1 Si/$Al_2$), 35 wt % $Al_2O_3$ |

Figure 4A:
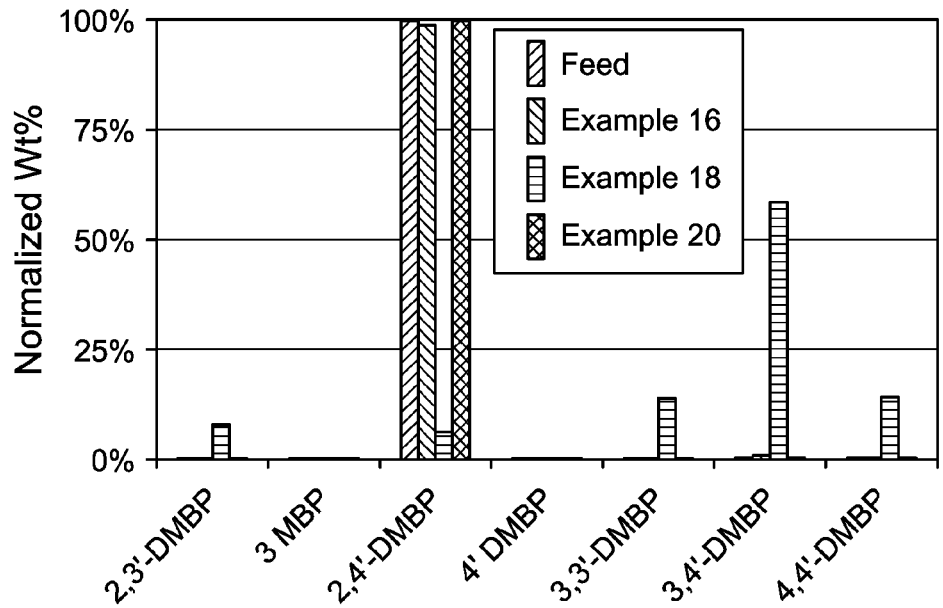
FIGS. 4(a) to (e) are bar graphs showing the normalized weight % of >C13 species in the reactor effluent of the DMBP isomerization experiments of Examples 16 to 21.
Figure 4B:
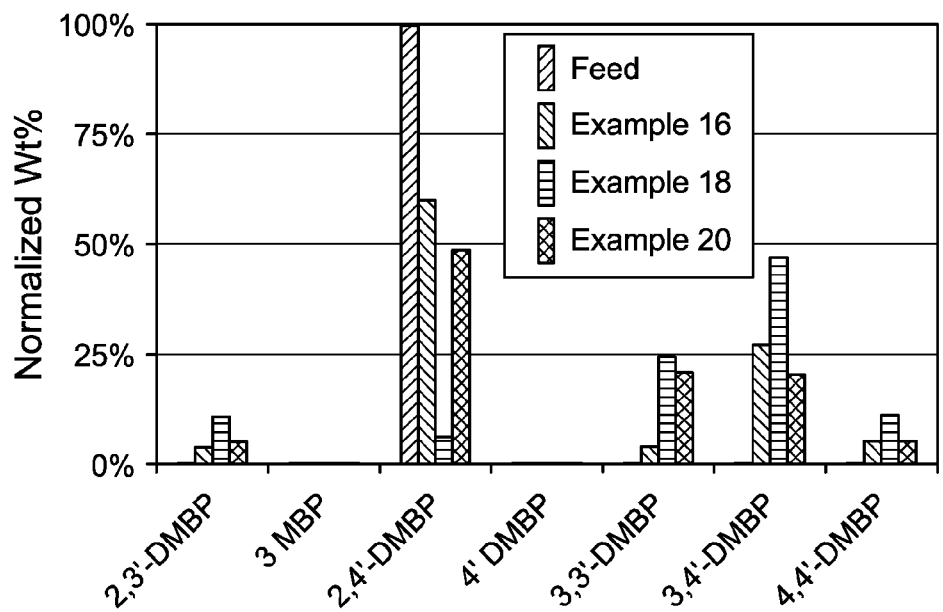

The catalysts of Examples 16, 18 and 20 were tested at 175° C. and 225° C. and the results are shown in FIGS. 4(a) and (b) respectively. The results show that the zeolite Beta catalyst was effective in the isomerization of 2,4' DMBP at both temperatures tested, whereas the TEA-mordenite of Example 19 was largely inactive at 175° C. but its activity improved at 225° C.

Figure 4C:
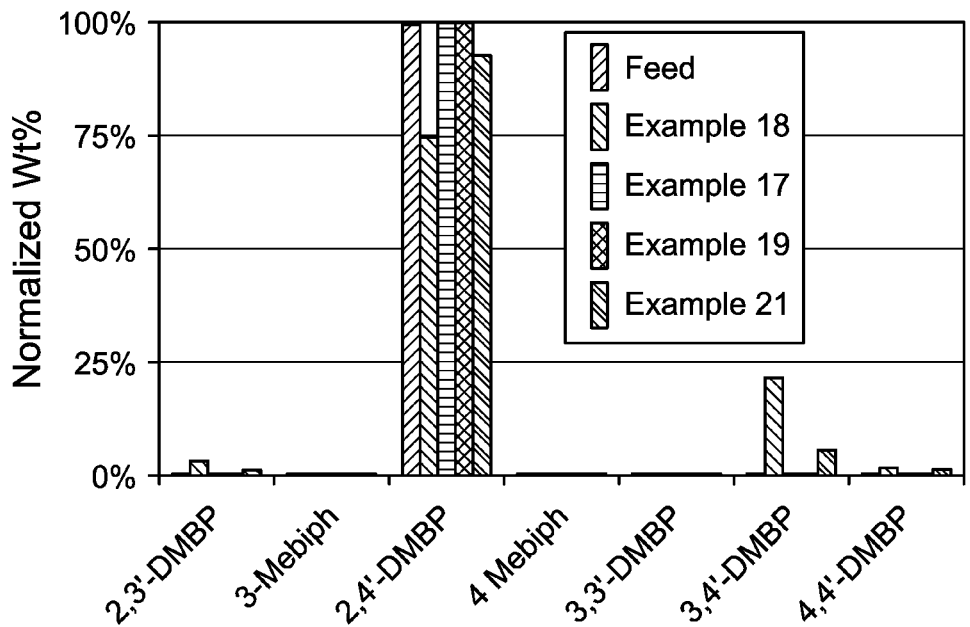
Figure 4D:
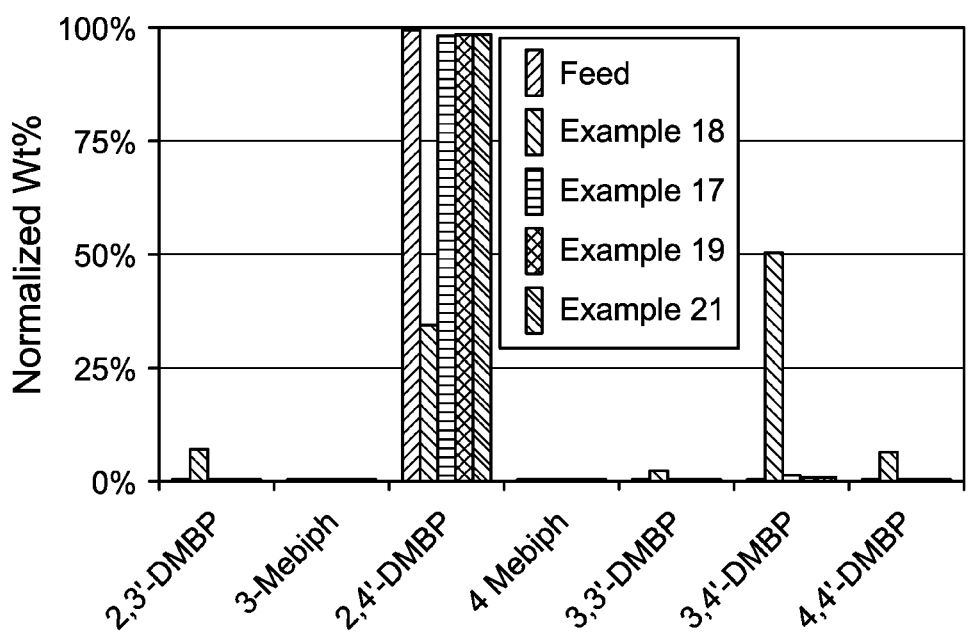
Figure 4E:
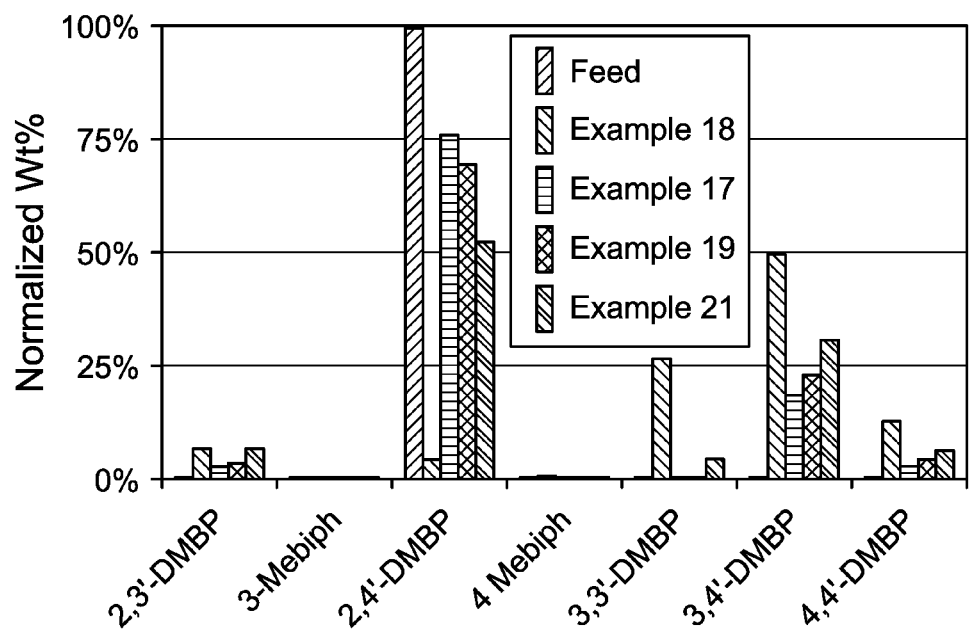

The catalysts of Examples 17, 18, 19 and 21 were tested at 135° C., 150° C. and 175° C. and the results are shown in FIGS. 4(c), (d) and (e) respectively. It will be seen that the zeolite beta catalyst exhibited significant isomerization activity even at temperatures as low as 135° C. Comparing the results in FIG. 4(a) with those in FIG. 4(e), it will be seen that at 175° C. the mordenite catalyst with the lower Si/$Al_2$ ratio (Example 21) exhibited higher isomerization activity than the mordenite catalyst with the higher Si/$Al_2$ ratio (Example 21).

The same trend (albeit lower in magnitude) is seen in going from the USY catalyst of Example 17 (CBV-760, 60:1 Si/$Al_2$) to that of Example 19 (CBV-720, 30:1 Si/$Al_2$).

Examples 22 to 25: Catalyst Screening with Surrogate Feed

In order to investigate the isomerization versus cracking activity of different catalysts in the presence of a cycloalkane, a study was conducted using a surrogate feed comprising a synthetic mixture of o-xylene, methylcyclohexane (MCH) and toluene having the composition shown in Table 4.

TABLE 4

| Component | Content (wt %) |
| --- | --- |
| Methylcyclohexane (MCH) | 30.4 |
| Toluene | 10.9 |
| o-Xylene | 58.4 |
| m-Xylene | <0.1 |
| p-Xylene | <0.2 |
| Unidentified | <0.1 |

Methylcyclohexane was included in the surrogate feed to assess the extent of the cracking side reaction and was used as an indicator for the expected extent of MCHT cracking in the case of DMBP/MCHT mixtures. Toluene was added to the feed to keep track of the toluene disproportionation activity of the catalysts. The catalyst samples tested are listed in Table 5 below and all are the pure zeolite crystals, pelletized and crushed and sieved down to 0.4-0.6 mm particles.

TABLE 5

| Example | Catalyst |
| --- | --- |
| 22 | H-mordenite (19:1 Si/$Al_2$) |
| 23 | H-ZSM-5 (56:1 Si/$Al_2$) |
| 24 | H-USY (30:1 Si/$Al_2$) |
| 25 | H-MCM-49 (19:1 Si/$Al_2$) |

The experiments were carried out in a fixed bed reactor system containing approximately 2 g of catalyst diluted with 0.1-0.2 mm SiC at 2 $h^{-1}$ weight-hourly-space-velocity (WHSV) and a pressure of 15 barg (liquid phase conditions). Before introducing the feed to the reactors, the catalysts were pretreated in $N_2$ flow at 300° C. for 24 h (heating ramp ~5° C./min) The performance of the samples in o-xylene isomerization was assessed in a fixed temperature program with set points at 165, 190, 210 and 230° C. and a dwell time of 48 h at each of these temperatures. After completing the experiment, the catalysts were subjected to another heat treatment in $N_2$ flow at 300° C. for 24 h and the entire experiment was repeated. The conversion and selectivity were measured by an on-line gas chromatograph, equipped with a high polarity FFAP column (50 m length, 0.32 mm ID, 0.50 µm df).

Figure 5:
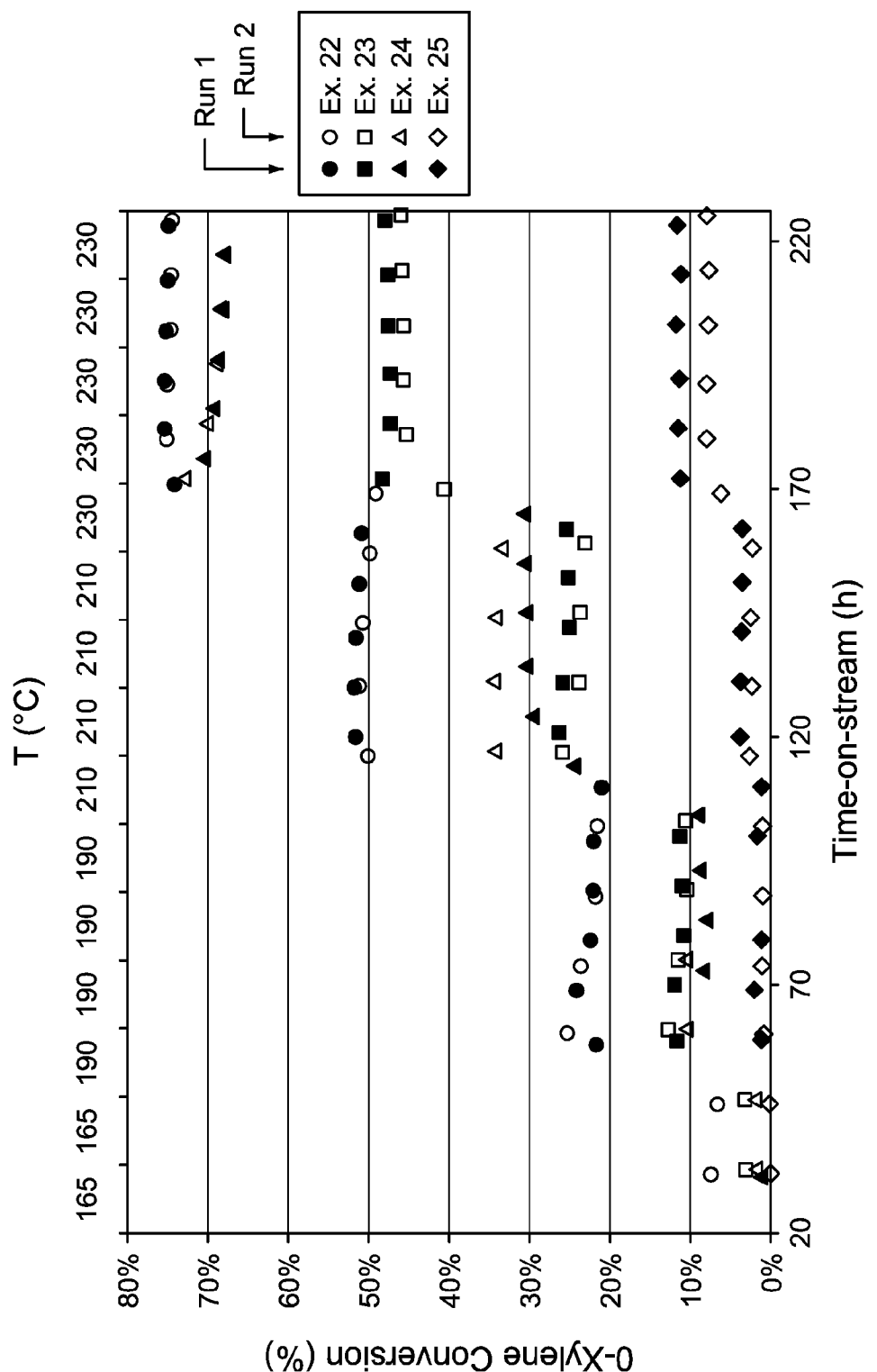
FIG. 5 is a graph of o-xylene conversion against temperature and time on stream for the o-xylene isomerization experiments of Examples 22 to 25.
Figure 6:
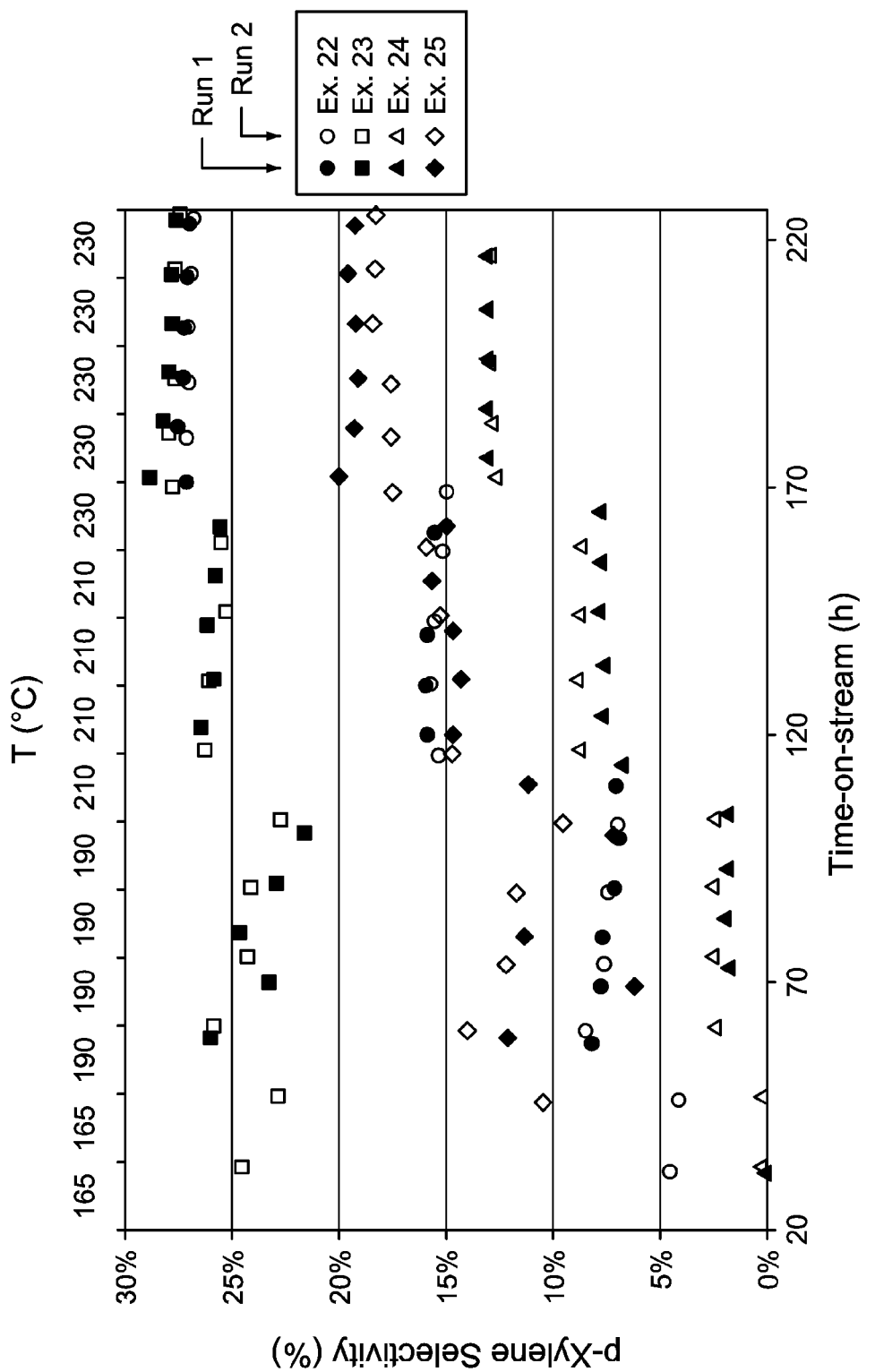
FIG. 6 is a graph of p-xylene selectivity against temperature and time on stream for the o-xylene isomerization experiments of Examples 22 to 25.

FIGS. 5 and 6 show the observed o-xylene conversion and p-xylene selectivity as a function of temperature and time-on-stream for the catalysts listed in Table 5. In FIGS. 5 and 6, squares indicate data from 1$^{st}$ run, circles indicate data from 2nd run, after regeneration in $N_2$. As the conversion of o-xylene is limited by thermodynamic equilibrium of the o, m, p-xylene mixture, another useful indicator of catalyst performance is the p-xylene approach to equilibrium (PXAE), which is defined as follows:

PXAE=(p-Xylene/Total Xylenes*100%)$_{product}$-(p-Xylene/Total Xylenes*100%)$_{feed}$/((p-Xylene/Total Xylenes*100%)$_{equilibrium}$-(p-Xylene/Total Xylenes*100%)$_{feed}$);

where % p-Xylene at equilibrium=((21.1+((1631.27)/(T(° C.)+273))/100)*100%

Figure 7:
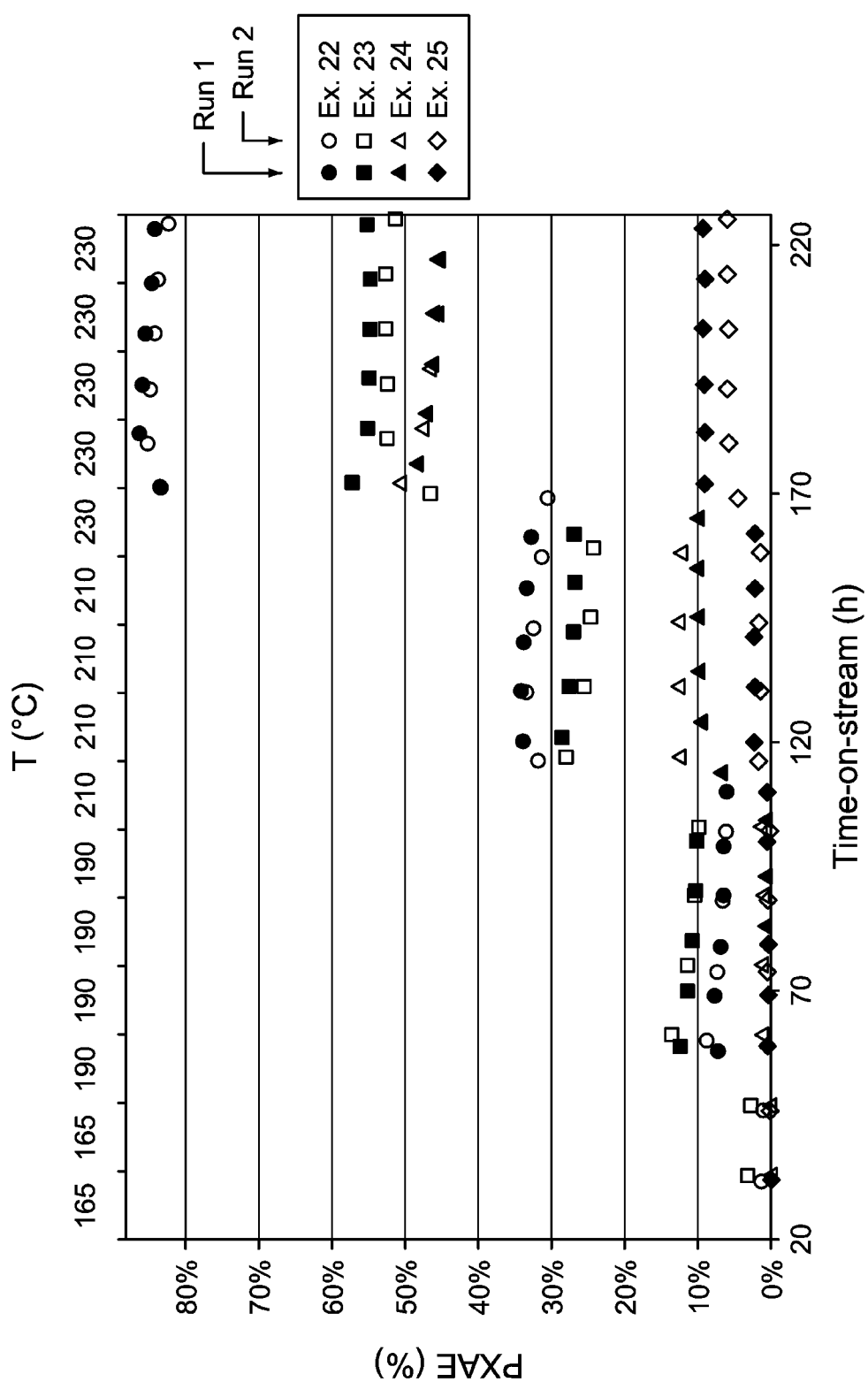
FIG. 7 is a graph of p-xylene approach to equilibrium against temperature and time on stream for the o-xylene isomerization experiments of Examples 22 to 25.

The PXAE results for the catalysts listed in Table 5 are shown in FIG. 7 (in which squares indicate data from 1$^{st}$ run, circles indicate data from 2nd run, after regeneration in $N_2$).

The results show that at each temperature the H-MOR catalyst exhibits superior o-xylene conversion as compared to the other catalysts tested. The p-xylene selectivity of the H-MOR catalyst is, however, generally somewhat lower up to 210° C. and m-xylene selectivity is higher. Nevertheless, the performance of H-MOR, as expressed by PXAE, surpasses the H-ZSM-5 catalyst above 190° C., whereas the p-xylene selectivity at 230° C. was equal for H-MOR and H-ZSM-5 catalysts. The H-MOR catalyst showed generally good stability over the time frame of the experiments and the loss of activity between the first and second runs was negligible. The H-ZSM-5 catalyst, on the other hand, did show slightly lower activity, and as a result lower PXAE, in the second run as compared to the first run.

Figure 8:
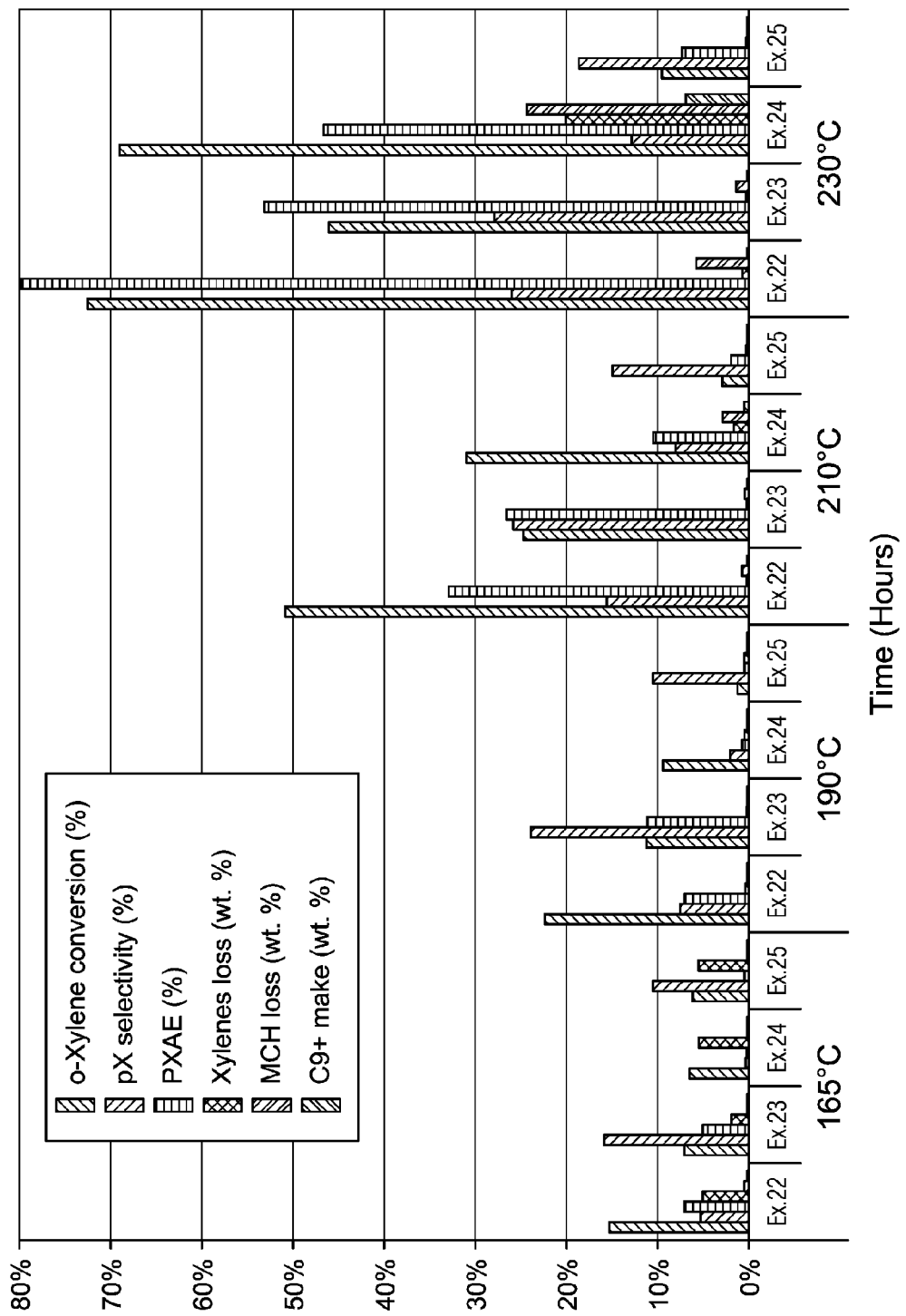
FIG. 8 is a graph summarizing the performance of the o-xylene isomerization catalysts tested in Examples 22 to 25 at temperatures of 165, 190, 210 and 230° C.

Tables 6 to 8 show the catalyst performance indicators averaged over the two runs for the experiments at 190, 210° C. and 230° C., respectively, whereas FIG. 8 summarizes the results over all four temperatures tested. In general, the H-USY and H-MCM-49 catalysts showed reduced performance as compared with the H-MOR and H-ZSM-5 materials. The H-USY catalyst showed high o-xylene conversion but relatively high loss of MCH (cracking) and $C_{9+}$ heavies make, which would be undesirable in the DMBP/MCHT application. The H-MCM-49 catalyst showed acceptable p-xylene selectivity but low activity over the range of experimental conditions tested.

TABLE 6 o-Xylene isomerization performance at 190° C.

| | Ex. 22 | Ex. 23 | Ex. 24 | Ex. 25 |
|---|---|---|---|---|
| Catalyst | H-MOR | H-ZSM-5 | H-USY | H-MCM-49 |
| T (° C.) | 210 | 210 | 210 | 210 |
| P (barg) | 15 | 15 | 15 | 15 |
| WHSV (h$^{-1}$) | 2 | 2 | 2 | 2 |
| o-Xylene Conversion (%) | 22.4 | 11.4 | 9.4 | 1.3 |
| p-Xylene/Total Xylenes (%) | 7.5 | 24.0 | 2.1 | 10.6 |
| PXAE (%) | 6.9 | 11.2 | 0.8 | 0.5 |
| Xylenes loss (wt. %) | 0.3 | 0.2 | 0.4 | 0.4 |
| MCH loss (wt. %) | 0.2 | 0.2 | 0.1 | <0.1 |
| C9+ make (wt. %) | <0.1 | <0.1 | 0.1 | <0.1 |

TABLE 7 o-Xylene isomerization performance at 210° C.

| | Ex. 22 | Ex. 23 | Ex. 24 | Ex. 25 |
|---|---|---|---|---|
| Catalyst | H-MOR | H-ZSM-5 | H-USY | H-MCM-49 |
| T (° C.) | 210 | 210 | 210 | 210 |
| P (barg) | 15 | 15 | 15 | 15 |
| WHSV (h$^{-1}$) | 2 | 2 | 2 | 2 |
| o-Xylene Conversion (%) | 51.1 | 25.0 | 31.8 | 3.1 |
| p-Xylene/Total Xylenes (%) | 15.7 | 25.9 | 8.2 | 15.1 |
| PXAE (%) | 33.0 | 26.6 | 10.9 | 1.9 |
| Xylenes loss (wt. %) | 0.2 | 0.1 | 1.7 | 0.2 |
| MCH loss (wt. %) | 0.8 | 0.5 | 3.1 | <0.1 |
| $C_{9+}$ make (wt. %) | <0.1 | <0.1 | 0.6 | <0.1 |

TABLE 8 o-Xylene isomerization performance at 230° C.

| | Ex. 22 | Ex. 23 | Ex. 24 | Ex. 25 |
|---|---|---|---|---|
| Catalyst | H-MOR | H-ZSM-5 | H-USY | H-MCM-49 |
| T (° C.) | 230 | 230 | 230 | 230 |
| P (barg) | 15 | 15 | 15 | 15 |
| WHSV (h$^{-1}$) | 2 | 2 | 2 | 2 |
| o-Xylene Conversion (%) | 72.6 | 46.9 | 69.2 | 9.7 |
| p-Xylene/Total Xylenes (%) | 26.1 | 28.0 | 13.0 | 18.7 |
| PXAE (%) | 79.8 | 54.2 | 46.8 | 7.5 |
| Xylenes loss (wt. %) | 0.6 | <0.1 | 20.1 | <0.1 |
| MCH loss (wt. %) | 5.8 | 1.4 | 24.5 | 0.3 |
| $C_{9+}$ make (wt. %) | 0.2 | 0.1 | 7.0 | <0.1 |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention. All documents described herein are incorporated by reference herein, including any priority documents and/or testing procedures to the extent they are not inconsistent with this text. Likewise, the term "comprising" is considered synonymous with the term "including," and whenever a composition, an element or a group of elements is preceded with the transitional phrase "comprising", it is understood that we also contemplate the same composition or group of elements with transitional phrases "consisting essentially of," "consisting of", "selected from the group consisting of," or "is" preceding the recitation of the composition, element, or elements and vice versa.

What is claimed is:

1. A process for producing 3,3', 3,4' and/or 4,4' dialkyl-biphenyl compounds, the process comprising:
   (a1) contacting a feed comprising one or more 2,X' dialkylbiphenyl isomers (where X' is 2', 3' and/or 4') with an acid catalyst under isomerization conditions effective to convert at least some of the 2,X' dialkyl-biphenyl isomers into one or more 3,3', 3,4' and 4,4' dialkylbiphenyl isomers and produce an isomerization effluent, where contacting (a1) is conducted at a temperature from 100° C. to 450° C. and a pressure from 2 to 7,000 kPa, wherein the contacting (a1) is conducted in the presence of a molecular sieve selected from the group consisting of BEA, FAU and MOR structure type molecular sieves and mixtures thereof;
   (b1) supplying at least part of the isomerization effluent to a separation zone to recover one or more of the 3,3', 3,4' and 4,4' dialkylbiphenyl isomers in the isomerization effluent and produce a residual fraction enriched in one or more of the 2,X' dialkylbiphenyl isomers as compared with the isomerization effluent;

(e1) recycling at least part of the residual fraction to the contacting (a1);

(d1) contacting toluene with hydrogen in the presence of a hydroalkylation catalyst under conditions effective to produce a hydroalkylation product comprising (methylcyclohexyl)toluenes;

(e1) dehydrogenating at least part of the hydroalkylation product under conditions effective to produce a dehydrogenation product comprising dimethylbiphenyl isomers and unreacted (methylcyclohexyl)toluenes;

(f1) supplying at least part of the dehydrogenation product to a separation zone to recover a first fraction enriched in one or more 3,3', 3,4' and/or 4,4' dimethylbiphenyl isomers as compared with the dehydrogenation product and a second fraction enriched in one or more 2,X' dimethylbiphenyl isomers as compared with the dehydrogenation product and also containing at least part of the unreacted (methylcyclohexyl)toluenes; and (g1) supplying at least part of the second fraction as at least part of the feed to the contacting (a1), wherein the dialkylbiphenyl isomers comprise dimethylbiphenyl isomers.

2. The process of claim 1, wherein the hydroalkylation catalyst comprises an acidic component and a hydrogenation component.

3. The process of claim 2, wherein the acidic component of the hydroalkylation catalyst comprises a molecular sieve selected from the group consisting of BEA and FAU structure type molecular sieves, molecular sieves of the MCM-22 family and mixtures thereof.

4. The process of claim 2, wherein the hydrogenation component of the hydroalkylation catalyst is selected from the group consisting of palladium, ruthenium, nickel, zinc, tin, cobalt, silver, gold, platinum and compounds and mixtures thereof.

5. The process of claim 1, wherein the conditions in the contacting (d1) include a temperature from 100° C. to 400° C. and a pressure from 10 to 7,000 kPa.

6. The process of claim 1, wherein the molar ratio of hydrogen to toluene supplied to the contacting (d1) is from 0.15:1 to 15:1.

7. The process of claim 1 and further comprising:

(h1) contacting biphenyl with a methylating agent in the presence of an alkylation catalyst under conditions effective to produce a methylation reaction product comprising a mixture of dimethyl-substituted biphenyl isomers;

(i1) supplying at least part of the methylation reaction product to a separation zone to recover a first fraction enriched in one or more 3,3', 3,4' and 4,4' dimethylbiphenyl isomers as compared with the methylation reaction product and a second fraction enriched in one or more 2,X' dimethylbiphenyl isomers as compared with the methylation reaction product; and (g1) supplying at least part of the second fraction as at least part of the feed to the contacting (a1).

8. The process of claim 7, wherein the biphenyl is produced by oxidative coupling of benzene.

9. The process of claim 7, wherein the biphenyl is produced by hydroalkylation of benzene to cyclohexylbenzene followed by dehydrogenation of the cyclohexylbenzene.

10. A process for producing 3,3', 3,4' and/or 4,4' dimethylbiphenyl compounds, the process comprising:

(a2) contacting toluene with hydrogen in the presence of a hydroalkylation catalyst under conditions effective to produce a hydroalkylation product comprising (methylcyclohexyl)toluenes;

(b2) dehydrogenating at least part of the hydroalkylation product under conditions effective to produce a dehydrogenation product comprising dimethylbiphenyl isomers and unreacted (methylcyclohexyl)toluenes;

(c2) separating the dehydrogenation product into a first fraction comprising one or more 3,3', 3,4' and 4,4' dimethylbiphenyl isomers and a second fraction comprising one or more 2,X' dimethylbiphenyl isomers (where X' is 2, 3 or 4) and at least part of the unreacted (methylcyclohexyl)toluenes;

(d2) contacting at least part of the second fraction with an acid catalyst under isomerization conditions effective to convert at least some of the 2,X' dimethylbiphenyl isomers into one or more 3,3', 3,4' and 4,4' dimethylbiphenyl isomers and produce an isomerization product; and (e2) recycling at least part of the isomerization product to the separating (c2).

11. The process of claim 10, wherein the hydroalkylation catalyst comprises an acidic component and a hydrogenation component, wherein the acidic component of the hydroalkylation catalyst comprises a molecular sieve, preferably selected from the group consisting of BEA and FAU structure type molecular sieves, molecular sieves of the MCM-22 family and mixtures thereof.

12. The process of claim 11, wherein the hydrogenation component of the hydroalkylation catalyst is selected from the group consisting of palladium, ruthenium, nickel, zinc, tin, cobalt, silver, gold, platinum and compounds and mixtures thereof.

13. The process of claim 10, wherein the conditions in the contacting (a2) include a temperature from 100° C. to 400° C. and a pressure from 10 to 7,000 kPa, and the molar ratio of hydrogen to toluene supplied to the contacting (a2) is from 0.15:1 to 15:1, and the contacting (d2) is conducted at a temperature from 100° C. to 450° C. and a pressure from 10 to 7,000 kPa and the contacting (d2) is conducted in the presence of a molecular sieve catalyst selected from the group consisting of BEA, FAU and MOR structure type molecular sieves and mixtures thereof.

14. The process of claim 10 and further comprising:

(f2) separating the first fraction into a third fraction enriched in one target isomer selected from 3,3', 3,4' and 4,4' dimethylbiphenyl and a fourth fraction depleted in said target isomer;

(g2) contacting at least part of the fourth fraction with an acid catalyst under isomerization conditions effective to produce an isomerization product having an increased concentration of the target isomer as compared with the fourth fraction; and (h2) recycling at least part of the isomerization product to the separating (f2).

15. A process for producing 3,3', 3,4' and/or 4,4' dimethylbiphenyl compounds, the process comprising:

(a3) contacting toluene with hydrogen in the presence of a hydroalkylation catalyst under conditions effective to produce a hydroalkylation product comprising (methylcyclohexyl)toluenes;

(b3) dehydrogenating at least part of the hydroalkylation product under conditions effective to produce a dehydrogenation product comprising dimethylbiphenyl isomers and unreacted (methylcyclohexyl)toluenes;

(c3) supplying at least part of the dehydrogenation product to a separation zone to recover a first fraction enriched in one or more 3,3', 3,4' and/or 4,4' dimethylbiphenyl isomers as compared with the dehydrogenation product and a second fraction enriched in one or more 2,X' dimethylbiphenyl isomers (where X' is 2', 3' and/or 4') as compared with the dehydrogenation product and also containing at least part of the unreacted (methylcyclohexyl)toluenes; and (d3) supplying at least part of the second fraction as at least part of a feed to an isomerization process comprising contacting the feed comprising one or more 2,X' dimethylbiphenyl isomers with an acid catalyst under isomerization conditions effective to convert at least some of the 2,X' dimethylbiphenyl isomers into one or more 3,3', 3,4' and 4,4' dimethylbiphenyl isomers and produce an isomerization effluent.

16. A process for producing 3,3', 3,4' and/or 4,4' dimethylbiphenyl compounds, the process comprising:

(a4) contacting biphenyl with a methylating agent in the presence of an alkylation catalyst under conditions effective to produce a methylation reaction product comprising a mixture of dimethyl-substituted biphenyl isomers;

(b4) supplying at least part of the methylation reaction product to a separation zone to recover a first fraction enriched in one or more 3,3', 3,4' and 4,4' dimethylbiphenyl isomers as compared with the methylation reaction product and a second fraction enriched in one or more 2,X' dimethylbiphenyl isomers (where X' is 2', 3' and/or 4') as compared with the methylation reaction product; and (c4) supplying at least part of the second fraction as at least part of a feed to an isomerization process comprising contacting the feed comprising one or more 2,X' dimethylbiphenyl isomers with an acid catalyst under isomerization conditions effective to convert at least some of the 2,X' dimethylbiphenyl isomers into one or more 3,3', 3,4' and 4,4' dimethylbiphenyl isomers and produce an isomerization effluent.

17. A process for producing 3,3', 3,4' and/or 4,4' dimethylbiphenyl compounds, the process comprising:

(a5) contacting toluene with hydrogen in the presence of a hydroalkylation catalyst under conditions effective to produce a hydroalkylation product comprising (methylcyclohexyl)toluenes;

(b5) dehydrogenating at least part of the hydroalkylation product under conditions effective to produce a dehydrogenation product comprising dimethylbiphenyl isomers and unreacted (methylcyclohexyl)toluenes;

(c5) separating the dehydrogenation product into a first fraction comprising one or more 3,3', 3,4' and 4,4' dimethylbiphenyl isomers and a second fraction comprising one or more 2,X' dimethylbiphenyl isomers (where X' is 2, 3 or 4) and at least part of the unreacted (methylcyclohexyl)toluenes;

(d5) contacting at least part of the second fraction with an acid catalyst under isomerization conditions effective to convert at least some of the 2,X' dimethylbiphenyl isomers into one or more 3,3', 3,4' and 4,4' dimethylbiphenyl isomers and produce an isomerization product;

(e5) recycling at least part of the isomerization product to the separating (c5);

(f5) optionally, separating the first fraction into a third fraction enriched in one target isomer selected from 3,3', 3,4' and 4,4' dimethylbiphenyl and a fourth fraction depleted in said target isomer;

(g5) contacting at least part of the fourth fraction with an acid catalyst under isomerization conditions effective to produce an isomerization product having an increased concentration of the target isomer as compared with the fourth fraction; and (h5) recycling at least part of the isomerization product to the separating (f5).

* * * * *